(12) United States Patent
Ben-Sasson

(10) Patent No.: US 7,037,891 B2
(45) Date of Patent: *May 2, 2006

(54) METHODS OF MODULATING G-PROTEIN-COUPLED RECEPTOR KINASE-ASSOCIATED SIGNAL TRANSDUCTION

(75) Inventor: Shmuel Ben-Sasson, Jerusalem (IL)

(73) Assignees: Children's Medical Center Corporation, Boston, MA (US); Yissum Research and Development, Jerusalem (IL)

( * ) Notice: Subject to any disclaimer, the term of this patent is extended or adjusted under 35 U.S.C. 154(b) by 230 days.

This patent is subject to a terminal disclaimer.

(21) Appl. No.: 10/012,035

(22) Filed: Dec. 11, 2001

(65) Prior Publication Data
US 2003/0004103 A1 Jan. 2, 2003

Related U.S. Application Data

(63) Continuation-in-part of application No. 09/735,274, filed as application No. PCT/US98/10319 on May 20, 1998, now abandoned, which is a continuation-in-part of application No. 08/861,338, filed on May 21, 1997, now Pat. No. 6,174,993.

(51) Int. Cl.
- *A01N 37/18* (2006.01)
- *A61K 38/00* (2006.01)
- *A61K 38/04* (2006.01)
- *C07K 16/00* (2006.01)
- *C07K 17/00* (2006.01)

(52) U.S. Cl. .................. 514/2; 530/326; 530/327; 530/328; 530/329; 530/330

(58) Field of Classification Search ................ 514/2
See application file for complete search history.

(56) References Cited

FOREIGN PATENT DOCUMENTS

| WO | WO 93/16703 A1 | 9/1993 |
| WO | WO 97/14038 A1 | 4/1997 |
| WO | WO 98/53050 A2 | 11/1998 |
| WO | WO 98/53051 A1 | 11/1998 |
| WO | WO 00/18895 A1 | 4/2000 |
| WO | WO 00/73469 A2 | 12/2000 |

OTHER PUBLICATIONS

Alemá et al, "Differentiation of PC12 phaeochromocytoma cells induced by v-src oncogene", *Nature* 316(6028):557-559 (1985).

Birchall et al, "Ro 32-0432, a Selective and Orally Active Inhibitor of Protein Kinase C Prevents T-Cell Activation", *J Parmacol Exp Ther* 268(2):922-929 (1994).

Bradshaw et al, "Therapeutic potential of protein kinase C inhibitors", *Agents Actions* 38(1-2):135-147 (1993).

Dudek et al, "Regulation of neuronal Survival by the Serine-Threonine Protein Kinase Akt", *Science* 275:661-665 (1997).

(Continued)

*Primary Examiner*—Robert S. Landsman
(74) *Attorney, Agent, or Firm*—Browdy and Neimark, PLLC

(57) ABSTRACT

The present invention concerns methods for the treatment of metabolic-related diseases by the modulation of GRK associated signal transduction. Preferred in accordance with the invention are modulators which comprise sequences derived from specific regions of the GRK.

29 Claims, 16 Drawing Sheets

βARK 1,2 SERINE/THREONINE KINASES

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| F | K | L | I | R | G | H | S | P | F  | R  | Q  | H  | K  | T  | K  | D  | K  | H  | E  |
| Y | Q | I | L | K | A |   | T |   | Y  | K  | E  |    | O  | S  | O  | N  | O  |    | Q  |
| W |   | M | M |   |   |   |   |   | W  |    | D  |    |    |    |    | D* |    |    | N  |
|   |   | V | V |   |   |   |   |   |    |    | N  |    |    |    |    | Q  |    |    | D  |
|   |   |   |   |   |   |   |   |   |    |    | E* |    |    |    |    | E  |    |    | D* |
|   |   |   |   |   |   |   |   |   |    |    | D* |    |    |    |    | E* |    |    | E* |

E* = a substituted or unsubstituted aliphatic, benzylic or aromatic ester of glutamic acid.
D* = a substituted or unsubstituted aliphatic, benzylic or aromatic ester of aspartic acid.

OTHER PUBLICATIONS

Franke et al, "P13K: Downstream AKTion Blocks Apoptosis", *Cell* 88:435-437 (1997).

Freedman et al, "Desensitization of G Protein-Coupled Receptors", *Recent Prog Horm Res* 51:319-353 (1996).

Ghiso et al, "Binding of Cystatin C to C4: The Importance of Sense-Antisense Peptides in their Interaction", *Proc Nat Acad Sci USA* 87(4):1288-1294 (1990).

Glover et al, "Polo-Kinase: The Choreographer of the Mitotic Stage?", *J Cell Biol* 135:1681-1684 (1996).

Hanks et al, The Eukaryotic Protein Kinase Superfamily in *The Protein Kinase Facts Book,* vol. I, Hardie et al, eds., Academic Press, Chapter 2 (1995).

Hemmings BA, "Akt Signaling: Linking Membrane Events to Life and Death Decisions", *Science* 275:628-631 (1997).

Hubbard et al, "Crystal structure of the tyrosine kinase domain of the human insulin receptor", *Nature* 372:746-753 (1994).

Kallunki et al. "JNK2 contains a specificity-determining region responsible for efficient c-Jun binding and phosphorylation", *Genes & Development* 8:2996-3007 (1994).

Kohn et al, Expression of a Constitutitively Active Akt Ser/Thr Kinase in 3T3-L1 Adipocytes Stimulates Glucose Uptake and Glucose Transporter 4 Translocation *J Biol Chem* 271(49):31372-31378 (1996).

Lange-Carter et al, "A Divergence in the MAP Kinase Regulatory Network efined by MEK Kinase and Raf", *Science* 260:315-318 (1993).

Lovrić et al, "Activation of Mil/Raf protein kinases in mitotic cells", *Oncogene* 12:1109-1116 (1996).

Mason IJ, "Th Ins and Outs of Fibroblast Growth Factors", *Cell* 78:547-552 (1994).

McMurray et al, "Cyclic peptide substrates of pp60c-src: synthesis and evaluation", *Int J Pept Protein Res* 42(3):209-215 (1993) (from *Chem Abastracts* 1993, Acc. No. 120: 100177).

Mohammadi et al, "Structure of the FGF Receptor Tyrosine Kinase Domain Reveals a Novel Autoinhibitory Mechanism", *Cell* 86:577=587 (1996).

Nishizuka Y, "Protein kinase C and lipd signaling for sustained cellular responses", *FASEB J* 9:484-496 (1995).

Okada et al, "Synthesis of Gin-Val-Val-Ala-Gly, a common sequence of thiol proteinase inhibitors, and its derivatives. Relationship between structure and effect on thiol proteinases", *Pept Chem* 653-656 (1998) (from *Chem Abstracts,* 1998, Acc. No. 109:69322).

Simmons et al, "Identification of an early-growth-response gene encoding a novel putative protein kinase", *Mol Cel Biol* 12(9):4164-4169 (1992).

Taylor et al, "cAMP-dependent protein kinase defines a family of enzymes", *Phil Trans R Soc Lond B* 340:315-324 (1993).

βARK 1,2 SERINE/THREONINE KINASES

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| F | K | L | I | R | G | H | S | P | F  | R  | Q  | H  | K  | T  | K  | D  | K  | H  | E  |
|   | O | V | L | K | A |   | T |   | Y  | K  | E  |    | O  | S  | O  | N  | O  |    | Q  |
| W |   | M | M |   |   |   |   |   | W  |    | D  |    |    |    |    | D* |    |    | N  |
|   |   | V | V |   |   |   |   |   |    |    | N  |    |    |    |    | Q  |    |    | D  |
|   |   |   |   |   |   |   |   |   |    |    | E* |    |    |    |    | E  |    |    | D* |
|   |   |   |   |   |   |   |   |   |    |    | D* |    |    |    |    | E* |    |    | E* |

E* = a substituted or unsubstituted aliphatic, benzylic or aromatic ester of glutamic acid.
D* = a substituted or unsubstituted aliphatic, benzylic or aromatic ester of aspartic acid.

FIG. 1

FIG. 2 bARK1

| ID | Mod | | | | | | | | | |
|---|---|---|---|---|---|---|---|---|---|---|
| K024H001 | Acetyl | L | L | R | G | H | S | | | |
| K024H003 | Acetyl | L | L | R | K* | H | S | | | |
| K024H007 | Acetyl | L | L | R | R* | H | S | | | |
| K024H101 | Myristyl-G | L | L | R | G | H | S | | | |
| K024H102 | Myristyl-G | L | L | R | G | H | S | P | F | R |
| K024H103 | Myristyl-G | L | L | R | K* | H | S | | | |
| K024H104 | Myristyl-G | L | L | R | E* | H | S | | | |
| K024H105 | Myristyl-G | L | L | R | Y* | H | S | | | |
| K024H106 | Myristyl-G | L | L | R | L* | H | S | | | |
| K024H107 | Myristyl-G | L | L | R | R* | H | S | | | |
| K024H108 | Myristyl-G | L | L | R | R* | H | S | K$ | | |
| K024H109 | Myristyl-G | L | L | R | K* | H | S | P | | |
| K024H110 | Myristyl-G | L | L | R | R* | H | S | I | V | T |
| K024H111 | Myristyl-G | L | L | R | R* | H | S | I | V | |
| K024H112 | Myristyl-G | L | L | R | R* | H | S | I | | |
| K024H113 | Myristyl-G | L | L | R | R* | H | S | K+ | | |
| K024H114 | Oleyl-G | L | L | R | R* | H | S | K+ | | |
| K024H901 | Stearyl-G | L | L | R | G | H | S | | | |
| K024H903 | Stearyl-G | L | L | R | K* | H | S | | | |

E* = D-isomer of glutamic acid
K* = D-isomer of lysine
K+ = Benzoylamide of lysine
K$ = Biotinylated lysine
L* = D-isomer of leucine
R* = D-isomer of arginine
Y* = D-isomer of tyrosine

US 7,037,891 B2

METHODS OF MODULATING G-PROTEIN-COUPLED RECEPTOR KINASE-ASSOCIATED SIGNAL TRANSDUCTION

CROSS-REFERENCE TO RELATED APPLICATIONS

This application is a continuation-in-part of U.S. application Ser. No. 09/735,274, filed Dec. 11, 2000, now abandoned, which is a 371 national stage application of PCT International Application No. PCT/US98/10319 filed May 20, 1998, which PCT International Application is a continuation-in-part of U.S. application Ser. No. 08/861,338, filed May 21, 1997, now issued as U.S. Pat. No. 6,174,993. The entire teachings of the above applications are incorporated herein by reference.

BACKGROUND OF THE INVENTION

Serine/threonine kinases are members of the eukaryotic protein kinase superfamily. Enzymes of this class specifically phosphorylate serine or threonine residues of intracellular proteins and are important in mediating signal transduction in multicellular organisms. Many serine/threonine kinases occur as intracellular proteins which take part in signal transduction within the cell, including signal transduction to the nucleus and the activation of other proteins.

As such, phosphorylation of serine or threonine by serine/threonine kinases is an important mechanism for regulating intracellular events in response to environmental changes. A wide variety of cellular events are regulated by serine/threonine kinases. A few examples include the ability of cells to enter and/or complete mitosis, cellular proliferation, cellular differentiation, the control of fat metabolism, immune responses, inflammatory responses and the control of glycogen metabolism.

An important superfamily of cell membrane receptors is the group known as G-protein coupled receptors (GPCR), known also as seven trans-membrane receptors (7TM). This superfamily of receptors is involved in the transmission of signals that originate from low molecular weight ligands such as adrenaline or from peptide ligands such as chemokines and a variety of hormones such as melanocyte stimulating hormone (MSH).

Numerous studies have shown that intracellular protein kinases which specifically interact with various members of the 7TM receptors are able to desensitize them and thereby decrease or eliminate the signal transmission effected 7TM. These protein kinases are known as G-protein-coupled receptor kinases (GRKs), which are serine/threonine kinases. So far, six of these kinases have been discovered (GRK1–6). Some of the GRKs are restricted to a small number of tissues (e.g., GRK1), while GRK2 and GRK 3, known also as β-ARK1 and β-ARK2 are ubiquitously expressed. A comprehensive review is provided, for example, by M. Bunemann and M. M. Hosey, "G-Protein Coupled Receptor Kinases as Modulators of G-Protein Signalling," *J of Physiology*, Vol. 517(1):5–23 (1999).

Syndrome X is a term coined in 1988 by Stanford University Endocrinologist Dr. Gerald Risson, that describes a group of symptoms including: high blood pressure, abdominal obesity, insulin resistance, high levels of triglycerides and low levels of HDL, low levels of anti-oxidant vitamins and DHEA, high cortisone levels, as well as depression. Some experts estimate that as many as two-thirds of Americans may be suffering from syndrome X, although it may be effectively hidden for years masquerading as symptoms for other conditions such as fatigue, poor mental concentration, abdominal obesity, edema, nerve damage and intense craving for sweets.

SUMMARY OF THE INVENTION

The present invention is based on the surprising finding that short peptides, corresponding to short sequences from specific regions of GRK, or variants of said sequences, were able to modulate melanogenesis in vitro, were able to decrease glucose levels in an animal model of diabetes, and were able to reduce weight and appetite in normal animals. The present invention is further based on the realization that the above peptides modulate the GRK-associated signal transduction (GAST). These two findings led to the realization that modulation of GRK associated signal transduction can alleviate a plurality of metabolic-related disorders and diseases.

Thus, by a first aspect, the present invention concerns a method for the modulation of metabolic parameters by administering to a subject in need of such modulation a compound comprising an amino acid sequence that corresponds to sequences in specific regions of GRK (hereinafter: the "HJ-loop, B4–B5 region, αD region, A-region") or to variants of said sequence.

The treatment of metabolism may be for the treatment of a plurality of diseases and disorders including: diabetes both Type I and Type II, but especially type II), obesity (by increase of metabolism and/or decrease of appetite or both), hypertension, dislipidemia (which includes increased LDL, increased cholesterol, decreased HDL, abnormal LDL), congestive heart failure, as well as other manifestations of syndrome X, such as low levels of anti-oxidant vitamins and DHEA, high cortisone levels, as well as depression.

The present invention further concerns methods for identifying the variants of said sequences effective in the treatment of metabolic diseases.

By a second aspect, the present invention concerns a method for modulating Diabetic-associated phenomena in an individual by administration to the individual at least one modulator of GAST.

The term "diabetic associated phenomena" relates to those parameters caused by diabetes and in particular diabetes type II such as: elevated blood glucose levels, diabesity (diabetic-associated obesity), diabetic related hypertension and diabetic associated dislipidemia.

The inhibitors of GAST may be compounds comprising amino acid sequences corresponding to sequences present in the above specific regions of the GRK, or variants of said sequences; antisense sequences corresponding to a portion of the GRK gene or GRK mRNA sufficient for reducing protein expression; dominant negative GRK's; ribozymes capable of specifically cleaving GRK RNA; and small organic molecules capable of inhibiting GAST.

The most preferred inhibitors of the GAST, in accordance with the present invention, are compounds which comprise short amino acid sequences corresponding to sequences present in the above specific regions of a GRK, or variants of said sequence. More preferably the specific region is the HJ-loop as will be explained below.

Without wishing to be bound by theory, it is assumed that the amino acid sequences present in the compounds of the invention mimics specific regions in the GRK, that are responsible for interactions with other cellular components, such as with the substrates of the GRK, phosphatases of the GRK, or other kinases that dephosphorylate, or phosphorylate, respectively, the GRK. In particular, it is assumed that the sequence binds to the GPCRs, which is the most relevant substrate of GRK. This mimic sequence is assumed to bind to the other cellular components (for example to the substrate of the GRK) and this binding cause the interruption of the interaction of the GRK with said cellular component. This interruption causes the modulation of the signal transduction mediated by the GRK.

Where originally the interaction between the GRK and the cellular component causes an "on" reaction (for example the cellular component is a phosphatase that inhibits the GRK activity, and thus may cause a stop in the GPCR desensitization activity and prolong the activity of GPCR and increase the overall signal transduction) said interruption causes inhibition of the signal transduction associated with the kinase—i.e. inhibition of the GPCR-associated activity. Where the interaction between the kinase and the cellular component is an "off" reaction (for example where phosphorylization of the GPCR by the GRK enzyme causes desensitization of the receptor, this leading to a decrease in the GRK physiological activity) said interruption decreases the "off" direction resulting in an overall increase in the signal transduction associated with the kinase—for example increased melanogenesis, increased glucose update, etc.

GENERAL DESCRIPTION OF THE INVENTION

By one aspect, the present invention concerns a method for the modulation of a metabolic parameter in a subject the method comprising:

administering to a subject in need of such treatment a therapeutically effective amount of a compound comprising a sequence selected from:
 (a) a sequence which is a continuous stretch of at least five amino acids present in GRK in positions 382–414 (HJ loop);
 (b) a sequence which is a continuous stretch of at least five amino acids present in GRK in positions 271–290 (αD region);
 (c) a sequence which is a continuous stretch of at least five amino acids present in GRK in positions 257–265 (B4–B5 region);
 (d) a sequence which is a continuous stretch of at least five amino acids present in a native GRK from positions 240–260 (A-region);
 (e) a variant of a sequence according to any one of (a) to (d) wherein up to 40% amino acids of the native sequence have been replaced with a naturally or non-naturally occurring amino acid or with a peptidomimetic organic moiety; and/or up to 40% of the amino acids have their side chains chemically modified; and/or up to 20% of the amino acids have been deleted, provided that at least 50% of the amino acids present in the sequences of (a) to (d) are unaltered in the variant and provided that the variant maintains the biological property of the parent amino acid sequences of (a) to (d);
 (f) a sequence of any one of (a) to (e) wherein at least one of the amino acids is replaced by the corresponding D-amino acid;
 (g) sequences according to any one of (a) to (f) wherein at least one peptidic backbone has been altered to a non-naturally occurring peptidic backbone;
 (h) a sequence being the sequence of any one of (a) to (g) in reverse order; and
 (i) a combination of two or more of the sequences of (a) to (h).

The term "modulation" refers to increase or decrease of the metabolic parameter tested, for example, decrease in blood glucose, decrease in appetite, decrease in weight, increase in melanogenesis, increase in basal metabolism etc. This term also refers to a change in the response of the metabolic parameter to effectors, such as a change in the level of blood glucose (the metabolic parameter) in response to effectors (for example, insulin administration, stress, glucose loading) as compared to control.

The term "metabolic parameter" refers to at least one measurable physiological phenomena which can be indicative of the activity of a metabolic pathway. The following table will give a list of metabolic parameters that can be modulated by the method of the invention, and the disease that may be treated by modulation of the parameter.

| Metabolic Parameter | Disease |
| --- | --- |
| Glucose level or insulin level | Diabetes (type I or II) |
| Plasma lipid profile (HDL level, cholesterol level, LDL level, HDL/LDL/ratio total lipid profile | Arteriosclerosis, cholesterolinemia hyerlipidemia, dislipidemia |
| Blood pressure | Hypertension |
| Abnormalities in blood coagulation/higher plasmonogen activator inhibitor Type I and fibrinogen levels | Coagulation disorders - especially associated with syndrome X |
| Albumin or protein in urine | Hyperuricemica/micro albumenia |
| Presence of cysts in ovaries | Polycystic ovarian syndrome |
| Food consumption | Obesity-(Syndrome X) |
| Change in body weight | Obesity-(Syndrome X) |
| Basal metabolic rate | Obesity-(Syndrome X) |

Modulation of an individual's metabolism refers to an inhibition or enhancement of metabolic processes such as glucose uptake (insulin dependent or independent), lipid breakdown or synthesis, gluconeogenesis, glycogenolysis, cellular uptake of free fatty acids and triglycerides and cholesterol metabolism compared to a base line level for the individual, as known in the art.

In a preferred embodiment, "modulation of a metabolic parameter" refers to enhanced melanogenesis, alteration of Syndrome X, correction of Type II diabetes mellitus, improvement of heart function, relief of hypertension, improved blood lipid profile and lowered propensity for obesity. Methods of determining changes in these functions and activities are well known in the art and are further described below.

The term "compound (comprising sequence)" refers to a compound that includes within it any of the sequences of (a) to (i) as defined above. The compound may be composed mainly from amino acid residues, and in that case the amino acid component of the compounds should comprise no more than a total of about 30 amino acids. Where the compound is mainly an amino acid compound, it may comprise any one of the amino acid sequences of (a) to (h), a combination of two or more, preferably of three, most preferably of two, of the sequences of (a) to (h) linked to each other (either directly or via a spacer moiety). The compound may further comprise any one of the amino acid sequences, or combinations as described above (in (a) to (i) above), together with additional amino acids or additional amino acid sequences. The additional amino acids may be sequences from other regions of the GRK, for example, sequences that are present in the kinase vicinity of the regions, N-terminal or C-terminal to the sequences of (a) to (d), or sequences which are not present in the GRK but were included in the compound in order to improve various physiological properties, such as: penetration into cells (sequences which enhance penetration through membranes or barriers) ; decreased degradation or clearance; decreased repulsion by various cellular pumps; improved immunogenic activities; improved various modes of administration (such as attachment of various sequences which allow penetration through various barriers, through the gut, etc.); increased specificity; increased affinity; decreased toxicity; and the like. A specific example is the addition of the amino acid Gly, or of several Gly residues in tandem, to the N-terminal of the sequence.

The compound may also comprise non-amino acid moieties, such as for example, hydrophobic moieties (various linear, branched, cyclic, polycyclic or heterocyclic hydrocarbons and hydrocarbon derivatives) attached to the peptides of (a) to (i) to improve penetration; or various protecting groups, especially where the compound is linear, which are attached to the compound's terminals to decrease degradation. Chemical (non-amino acid) groups present in the compound may be included in order to improve various physiological properties such as penetration into cells (sequences which enhance penetration through membranes or barriers); decreased degradation or clearance; decreased repulsion by various cellular pumps; improved immunogenic activities; improvements in various modes of administration (such as attachment of various sequences which allow penetration through various barriers, through the gut, etc.); increased specificity; increased affinity; decreased toxicity; and the like. A specific example is the addition of the amino acid Gly, or of several Gly residues in tandem, to the N-terminal of the sequence. The chemical groups may serve as various spacers, placed, for example, between one or more of the above amino acid sequences, so as to spatially position them in suitable order in respect of each other.

The compound of the invention may be linear or cyclic, and cyclization may take place by any means known in the art. Where the compound is composed predominantly of amino acids/amino acid sequences, cyclization may be N- to C-terminal, N-terminal to side chain and N-terminal to backbone, C-terminal to side chain, C-terminal to backbone, side chain to backbone and side chain to side chain, as well as backbone to backbone cyclization. Cyclization of the compound may also take place through the non-amino acid organic moieties.

The association between the amino acid sequence component of the compound and other components (whether amino acid or non-amino acid) of the compound may be by covalent linking, by non-covalent complexion, for example, by complexion to a hydrophobic polymer, which can be degraded or cleaved producing a compound capable of sustained release; by entrapping the amino acid part of the compound in liposomes or micelles to produce the final compound of the invention. The association may be by the entrapment of the amino acid sequence within the other component (liposome, micelle) or the impregnation of the amino acid sequence within a polymer to give the final compound of the invention.

Preferably the compounds comprise an amino acid sequence of (a) to (h) above in association with (in the meaning described above) a moiety for transport across cellular membranes.

The term "moiety for transport across cellular membranes" refers to a chemical entity, or a composition of matter (comprising several entities) that causes the transport of members associated (see above) with it through phospholipidic membranes. One example of such moieties are hydrophobic moieties such as linear, branched, cyclic, polycyclic or heterocyclic substituted or non-substituted hydrocarbons. Another example of such a moiety is short peptides that cause transport of molecules attached to them into the cell by, gradient derived, active or facilitated transport. Other examples of other non-peptidic moieties known to be transported through membranes such as glycosylated steroid derivatives, are well known in the art. The moiety of the compound may be a polymer, liposome or micelle containing, entrapping or incorporating the amino acid sequence therein. In the above examples the compound of the invention is the polymer, liposome, micelle, etc., impregnated with the amino acid sequence.

The term "a sequence which is a continuous stretch of at least 5 amino acids present . . . " means any continuous stretch having a minimum of 5 amino acids to a maximum of the full length of the region, which are present within, or is the amino acid sequence described by reference to the specified positions of GRK. For example, in the HJ-loop defined as positions 382–414 of the GRK, the continuous stretch of at least 5 amino acids may be from amino acid at position 382 to 386, from 383 to 387, from 384 to 388, . . . 410–414. The continuous sequence may also be of 5, 6 (382 to 387 . . . 409 to 414), 7, 8, 9, 10, 11, 12, 13, 14, 15, 16, amino acids, obtained from each of these regions.

The term "GRK" in reference to specific positions concerns protein serine/threonine kinase GRK2 denoted as Accession No. 4501971 and GRK3 denoted as Accession No. 51939484 in NCB1 database.

The term "wherein up to 40% of amino acids of the native sequence have been replaced with a naturally or non-naturally occurring amino acid or with a peptidomimetic organic moiety" in accordance with the present invention, concerns an amino acid sequence, which shares at least 60% of its amino acid with the native sequence as described in (a), (b), (c) or (d) above, but some of the amino acids were replaced either by other naturally occurring amino acids, (both conservative and non-conservative substitutions), by non-naturally occurring amino acids (both conservative and non-conservative substitutions) , or with organic moieties which serve either as true peptidomimetics (i.e., having the same steric and electrochemical properties as the replaced amino acid), or merely serve as spacers in lieu of an amino acid, so as to keep the spatial relations between the amino acids spanning this replaced amino acid. Guidelines for the determination of the replacements and substitutions are given in the detailed description part of the specification. Preferably, no more than 30%, 25% or 20% of the amino acids are replaced.

The term "wherein up to 40% of the amino acids have their side chains chemically modified" means that some amino acids are the residues as appearing in the native sequence that have been modified, typically by addition of a functional group. For example, chemical modification means that where the native sequence Thr appears, the variant di-iodo-Thr may appear. The modification may be carried out "in situ", i.e., on the native amino acid when present in the sequence. The modification may be by using a chemically modified amino acid residue X', in lieu of amino acid residue X in the process of preparation. Preferably, more than 30%, 25%, or 20% of the amino acids have their side chains chemically modified.

The term "up to 20% of the amino have been deleted" refers to an amino acid sequence which maintains at least 20% of its amino acid. Preferably no more than 10% of the amino acids are deleted, and more preferably none of the amino acids are deleted.

The term "provided that at least 50% of the amino acids present in the sequence of (a) to (d) are unaltered in the variant and provided that the variant maintains the biological properties of the parent amino acid sequence", the variant may be composed of a combination of replacements, chemical modifications and deletions so long as at least 50% of the amino acids are the same (in nature and in the position) as those in the parent sequence of (a) to (d). Furthermore, the variant should have the GAST modulating activities as the parent sequence (although possibly at a higher level).

It should be clear that since the variants merely interrupt protein-protein interaction, there is no need to mimic the full kinase region in order to cause such an interruption, as it is possible to mimic small subsequences from different parts of the kinase. In addition, there is no need to faithfully copy all the amino acids of the region and it is possible merely to mimic the spatial positioning and chemically those amino acids involved with the interaction.

When calculating , 40% (or 35, 30, 25, or 20%) replacement/substitution or 20% (or 10%) deletion from sequences, the number of actual amino acids should be rounded always mathematically so that 40% of an 11 mer sequence (4.4) is four amino acids and 40% of a 12 mer sequence (4.8) is five amino acids.

Typically "essential amino acids" are maintained, chemically modified or replaced by conservative substitutions while non-essential amino acids may be maintained, chemically modified, deleted or replaced by conservative or non-conservative replacements. Generally, essential amino acids as determined by various Structure-Activity-Relationship (SAR) techniques (for example amino acids when replaced by Ala cause loss of activity) are replaced by conservative substitution, while non-essential amino acids can be deleted or replaced by any type of substitution. Guidelines for the determination of the deletions, replacements and substitutions are given in the "Detailed Description" part of the specification.

The term "region" refers to a sequence in a specific location of the GRK that corresponds to the positions selected from: 382–414 (termed: HJ loop) ; positions 271–290 (termed: αD region); position 257–265 (termed: B4–B5 region) and position 240–260 (termed: A-region).

The term "corresponding D-amino acid" refers to the replacement of the naturally occurring L-configuration of the natural amino acid residue by the D-configuration of the same residue. In particular Gly residues should be replaced by D-amino acids and in particular D-lys or D-Arg.

The term "at least one peptidic backbone . . . non-naturally occurring peptidic backbone" means that the bond between the N- of one amino acid residue to the C- of the next has been altered to non-naturally occurring bonds by reduction (to —$CH_2$—NH—), alkylation (methylation) on the nitrogen atom, or the bonds have been replaced by amidic bond, urea bonds, or sulfonamide bond, etheric bond (—$CH_2$—O—), thioetheric bond (—$CH_2$—S—), or to —CS—NH—,; The side chain of the residue may be shifted to the backbone nitrogen to obtain N-alkylated-Gly (a peptidoid).

The term "in reverse order" refers to the fact that the sequence of (a) to (f) may have the order of the amino acids as it appears in the native GRK from N- to the C-direction, or may have the reversed order (as read in the C- to N-direction). For example, if a subsequence of the HJ-loop of GRK is SQHGVF (residues 14–19 of SEQ ID NO:22), a sequence in a reverse order is FVGHQS (SEQ ID NO:42). It has been found that many times sequences having such a reverse order can have the same properties in small peptides as the "correct" order, probably due to the fact that the side chains, and not the peptidic backbones, are the ones responsible for interaction with other cellular components. Particularly preferred, are what is termed "retro inverso" peptides—i.e., peptides that have both a reverse order as explained above, and in addition each and every single one of the amino acids, has been replaced by the non-naturally occurring D-amino acid counterpart, so that the net end result as regards the positioning of the side chains (the combination of reverse order and the change from L to D) is zero change. Such retro-inverso peptides, while having similar binding properties to the native peptide, were found to be resistant to degradation.

The present invention further concerns a method for the treatment of diabetes and diabetic-associated phenomena comprising administering to a subject in need of such treatment an effective amount of a compound comprising a sequence selected from:

(a) a sequence which is a continuous stretch of at least five amino acids present in GRK in positions 382–414 (HJ loop);

(b) a sequence which is a continuous stretch of at least five amino acids present in GRK in positions 271–290 (αD region);

(c) a sequence which is a continuous stretch of at least five amino acids present in GRK in positions 257–265 (B4–B5 region);

(d) a sequence which is a continuous stretch of at least five amino acids present in a native GRK in positions 240–260 (A-region);

(e) a variant of a sequence according to any one of (a) to (d) wherein up to 40% amino acids of the native sequence have been replaced with a naturally or non-naturally occurring amino acid or with a peptidomimetic organic moiety; and/or up to 40% of the amino acids have been chemically modified; and/or up to 20% of the amino acids have been deleted, provided that at least 50% of the amino acids present in the sequence of (a) to (d) are unaltered in the variant and provided that the variant maintains the biological property of the parent amino acid sequences of (a) to (d);

(f) a sequence of any one of (a) to (e) wherein at least one of the amino acids is replaced by the corresponding D-amino acid;

(g) a sequence according to any one of (a) to (f) wherein at least one peptidic backbone has been altered to a non-naturally occurring peptidic backbone;

(h) a sequence being the sequence of any one of (a) to (g) in reverse order; and (i) a combination of two or more of the sequences of (a) to (h).

The term "diabetes " in the context of the present invention concerns both diabetic mellitus Type II caused by insulin resistance and diabetic mellitus Type I caused by decrease of insulin secretion. In the latter case, there should be at least some intrinsic insulin concentration present in the subject's serum (as the compound works by GPCR pathway), either as a result of basal secretion or as a result of external administration. Thus, the compounds of the invention may be used together with insulin, thus lowering the required dosage, or decreasing the episodes of administration.

The term "treatment off diabetic-associated phenomena" includes: decrease in blood glucose levels, improved response (as regards control glucose blood levels) to effectors such as insulin administration, fasting or glucose loading, as well as improvement in at least one of diabetes-associated phenomena as described above including obesity, hypertension, dislipidemia and the like.

The present invention also concerns use of a compound comprising a sequence selected from:
  (a) a sequence which is a continuous stretch of at least five amino acids present in GRK in positions 382–414 (HJ loop);
  (b) a sequence which is a continuous stretch of at least five amino acids present in GRK in positions 271–290 (αD region);
  (c) a sequence which is a continuous stretch of at least five amino acids present in GRK in positions 257–265 (B4–B5 region);
  (d) a sequence which is a continuous stretch of at least five amino acids present in a native GRK in positions 240–260 (A-region);
  (e) a variant of a sequence according to any one of (a) to (d) wherein up to 40% amino acids of the native sequence have been replaced with a naturally or non-naturally occurring amino acid or with a peptidomimetic organic moiety; and/or up to 40% of the amino acids have their side chains chemically modified; and/or up to 20% of the amino acids have been deleted, provided that as at least 50% of the amino acids present in the sequence of (a) to (d) are unaltered in the variant and provided that the variant maintains the biological property of the parent amino acids of (a) to (d);
  (f) a sequence of any one of (a) to (e) wherein at least one of the amino acids is replaced by the corresponding D-amino acid;
  (g) sequences according to any one of (a) to (f) wherein at least one peptidic backbone has been altered to a non-naturally occurring peptidic backbone;
  (h) a sequence being the sequence of any one of (a) to (g) in reverse order; and
  (i) a combination of two or more of the sequences of (a) to (h).
for the preparation of a medicament for the treatment of a disease selected from: diabetes, hypertension, obesity, dislipidemia, congestive heart disease, arteriosclerosis, cholesterolinemia, coagulation disorders and syndrome X The present invention also concerns a method for obtaining the most favorable compounds comprising the above sequences (a) to (i), for the modulation of a metabolic parameter.

Thus the present invention concerns a method for obtaining compounds for the modulation of a metabolic parameter, the method comprising:
  (a) identifying peptide regions in GRK that are in positions selected from: 382–414 (HJ-loop), 271–290 (A-region), 257–265 (B4–B5 region), 240–260 (αD region);
  (b) synthesizing a plurality of compounds comprising a sequence selected from:
    (b1) a sequence corresponding to at least five continuous amino acid sequences of the HJ-loop, A-region, B4–B5 or αD region;
    (b2) a variant of a sequence according to (b1) wherein up to 40% amino acids of the native sequence have been replaced with a naturally or non-naturally occurring amino acid or with a peptidomimetic organic moiety; and/or up to 40% of the amino acids have their side chains chemically modified; and/or up to 20% of the amino acids have been deleted, provided that the variant has at least 50% of the amino acids present in the sequence of (b1) unaltered and that the variant maintains the biological property of the parent amino acids of(b1);
    (b3) a sequence of (b1) or (b2) wherein one or more of the amino acids has been replaced by the corresponding D-amino acid;
    (b4) a sequence of (b1), (b2) or (b3) wherein at least one peptidic backbone has been altered to a non-naturally occurring peptidic backbone;
    (b5) a sequence being the sequence of any one of (b1), (b2), (b3) or (b4) in a reverse order; and
    (b6) a combination of two or more sequences of (b1)–(b5);
  (c) testing the modulation activity of the compounds of (b) in a test assay for determining the level of at least one metabolic parameter;
  (d) selecting from the compounds of (c) those compounds which modulated the metabolic parameter in the test assay as compared to the modulation in the same test assay in the absence of the compound; and
  (e) producing the compounds of (d) thereby obtaining compounds for the modulation of the metabolic parameter.

Preferably, the amino acid sequence of (a) above should be in positions 382 to 414 of the GRK (HJ-loop), more preferably in positions 383 to 398 of the GRK. Preferably, the amino acids in positions (K)383, (R)386, (G)387, (H)388, (S)389, (R)392, (Q)393, (H)394, (T)396 and (K)399 should be either identical to the amino acids present in the native kinase, be chemically modified, or alternatively should be conservative substitutions of these amino acids (for the definition of conservative substitutions please refer to the Detailed Description of chemically modified).

The amount of compounds of the invention administered to the individual will depend on the type and severity of the disease (for example, the level of hyperinsulinemia) and on the characteristics of the individual, such as general health, age, body weight, sex and tolerance to drugs as well as on the mode of administration. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

By a second aspect the present invention concerns a method for the treatment of a diabetic-associated phenomena, comprising administering to a subject in need of such treatment a therapeutically effective amount of a GAST-modulator.

The term "diabetic-associated phenomena" refers to diabetes itself, in particular diabetes type II, as well as the directed undesirable manifestations caused by diabetes measured by determination of: blood glucose levels, diabesity (diabetic-associated obesity), diabetic related hypertension and diabetic associated dislipidemia.

Among the GAST modulators that can be employed are compounds comprising sequences derived from GRK regions responsible for interaction with cellular components, or variants of such sequences as described above; antibodies immunoreactive with GRK; anti-sense nucleic acids that block expression of GRK; negative-dominant GRK genes which express GRK proteins with reduced or non-existent biological activity, ribozymes capable of specifically cleaving GRK-RNA and small organic molecules. Any of these modulators of GAST will be able to improve the diabetic-associated phenomena and thus be suitable for treatment of a disease as described above.

Preferably the GAST modulators are compounds comprising sequences derived from regions of the GRK which are responsible for interaction with other cellular components, especially with the GPCR substrate. As indicated above, it is assumed that peptides mimicking said regions, bind to the cellular components (such as the GPCR substrate of the GRK), and by this interrupt the interaction of the GRK-kinase and the substrate, leading to modulation of GAST.

More specifically, the GAST modulator is selected from (i) a compound comprising a sequence selected from:
  (a) a sequence which is a continuous stretch of at least five amino acids present in GRK in positions 382–414 (HJ loop);
  (b) a sequence which is a continuous stretch of at least five amino acids present in GRK in positions 271–290 (αD region);
  (c) a sequence which is a continuous stretch of at least five amino acids present in GRK in positions 257–265 (B4–B5 region);
  (d) a sequence which is a continuous stretch of at least five amino acids present in a native GRK in positions 240–260 (A-region);
  (e) a variant of a sequence according to any one of (a) to (d) wherein up to 40% amino acids of the native sequence have been replaced with a naturally or non-naturally occurring amino acid or with a peptidomimetic organic moiety; and/or up to 40% of the amino acids have their side chains chemically modified; and/or up to 20% of the amino acids have been deleted, provided that at least 50% of the amino acids present in the sequence of (a) to (d) are unaltered in the variant, and that provided that the variant maintains the biological property of the parent amino acid sequences of (a) to (d);
  (f) a sequence of any one of (a) to (e) wherein at least one of the amino acids is replaced by the corresponding D-amino acid;
  (g) a sequence according to any one of (a) to (f) wherein at least one peptidic backbone has been altered to a non-naturally occurring peptidic backbone;
  (h) a sequence being the sequence of any one of (a) to (g) in reverse order; and
  (i) a combination of two or more of the sequences of (a) to (h);.
(ii) an antibody against GRK- or an immunogenic compound thereof;
(iii) antisense nucleic acid sequences complementary to a region in the GRK gene or GRK RNA, so that hybridization between said antisense and said gene, or hybridization between said antisense and said RNA results in decrease in expression of GRK;
(iv) ribozymes that specifically cleave GRK RNA;
(v) expression constructs coding for negative dominant GRK; and
(vi) small organic molecules Specific examples of the compounds of (i) are compounds which comprise any one of the sequences as specified in: K024H001 (SEQ ID NO.: 1), K024H003 (SEQ ID NO.: 2), K024H007 (SEQ ID NO.: 3), K024H101 (SEQ ID NO.: 4) K024H102 (SEQ ID NO.: 5) , K024H103 (SEQ ID NO.: 6), K024H104 (SEQ ID NO.: 7) , K024H105 (SEQ ID NO.: 8), K024H106 (SEQ ID NO.: 9), K024H107 (SEQ ID NO.: 10), K024H108 (SEQ ID NO.: 11) K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), or any one of SEQ ID NOS.:20 to 38 associated with a moiety for transfer across cellular membranes.

The term "GRK-associated signal transduction (GAST)" refers to the level of signaling mediated by that GPCR, which the GRK2 or GRK3 phosphorylates. Typically the level can be determined by determining the level of the phosphorylation of at least one substrate in the GRK-signaling pathway, which may be a direct substrate of GRK (GPCR receptors such as $\beta_{2/1}$-adrenergic receptor, $\alpha_2$-adrenergic receptor, acetylcholine receptor, opioid receptors, rhodopsin, $A_{(1,2,3}$ ₎purinergic receptor, synuclein, Angiotensin II 1a, $D_iA$-dopamine, N-formyl peptide, muscarinic receptor, platelet activating factor, thrombin etc (Bunemann et al, *J of Physiology* (1999) 517.1,5–23), or a substrate of another kinase more downstream in the GRK- kinase signaling pathway.

The sequences which correspond to regions of GRK, in addition to their ability to modulate a metabolic parameter also are useful for generating antibodies that can modulate GRK-associated signal transduction, thus modulating metabolism. The sequences act as antigenic agents for producing such antibodies. These antibodies, in turn, act as modulators of GAST, thereby modulating metabolism.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 is a table illustrating the amino acid sequences (SEQ ID NO:41) of the HJ loop of GRK2 and GRK3, also referred to herein as βARK1 and βARK2.

FIG. 2 is a table illustrating the sequences of peptides K024H001 (SEQ ID NO.: 1), K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H 108 (SEQ ID NO.: 11), K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19).

DETAILED DESCRIPTION OF THE INVENTION

Figure 3:
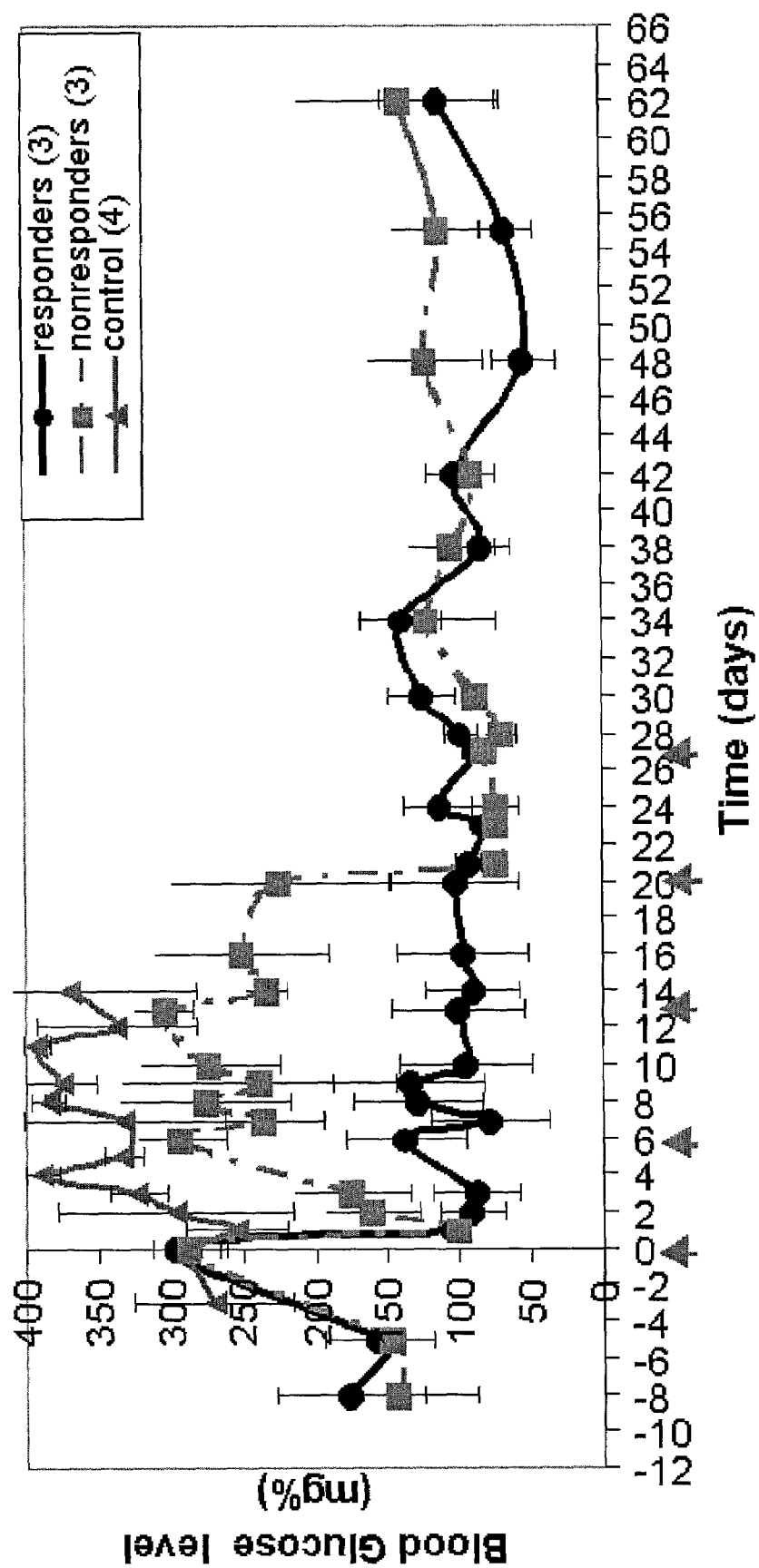
FIG. 3 is a graph that shows the effects of a single injection of the compound of the invention comprising a GRK-derived peptide on blood-glucose of sand rats (*psamomys obesus*).

It has been found in accordance with the present invention that modulation of activity of GAST influences a variety of signal-transduction pathways. For example, inhibition of a GAST, i.e. elimination of the agonist-dependent desensitizing activity caused by phosphorylation of the GPCR by the GRK, can result in a stronger or more extended signal by the relevant GPCR receptor; e.g., extending the duration of hormonal effects of, for example, adrenaline or any ligand activating the receptor. Thus, agents which modulate the activity of GAST can be used in the treatment of diseases that result from a lower bioavailability of the corresponding GPCR ligand, such as low availability of epinephrine, dopamine, angiotensin or any other GPCR-ligand.

A particular intriguing situation with this invention is the systemic administration of a GAST modulator. Under such circumstances, multiple systems can be affected simultaneously. Without wishing to be bound by a particular mechanism, it is believed that, if all of the systems which control the metabolic activity of the body are tuned by the same molecular mechanism, namely GRK activity, then a systemic inhibition of GRK2, GRK3 or its associated signal transduction pathway will have a simple phenotypic result: increase in the overall body basal metabolic rate due to elimination of GPCR desensitization and prolonging of its activity. Such a result is favorable in the condition now known as "syndrome-X" which is typified by the onset of type II diabetes mellitus, obesity and other conditions especially diabetic-associated phenomena. For a review of syndrome-X, see O. Timar et al., "Metabolic Syndrome X: A Review," Can. J. Cardiol, 16(6): 779–789 (2000).

With this invention, inhibiting the effects of GRK2, GRK3 which can be thought of as a metabolic regulator, is a method of treating type 2 diabetes mellitus (DM). It appears that in specific low calorie environments, organisms including humans, have evolved a mechanism by which maximal energy metabolism is achieved by down-regulating metabolic processes. It is postulated in this invention that the mechanism for this down-regulation is phosphorylation of β-adrenergic receptors (βAR) by GRK2 (β-adrenergic receptor kinase). The attenuated βAR leads to decreased signaling to significant metabolic processes such as glucose uptake (via insulin resistance), lipid breakdown, diabetic-associated obesity, diabetic associated hypertension, etc. This enables the organism to maintain energy homeostasis despite low exogenous caloric intake.

Nutritional diabetes can be caused by a pathologic function of the interaction between βAR and GRK2. When organisms that are maximally adapted to a low energy environment are transferred to a high-energy environment, they develop a metabolic syndrome characterized by type 2 diabetes mellitus (DM), hypertension, obesity, insulin resistance and other diabetic-associated phenomena as described above. This is due to the surfeit of energy, which is inefficiently utilized because of the low metabolic rate. The surplus energy is converted to fat and there is a hyperglycemia due to insulin resistance in the face of high glucose levels. By decreasing the activity of GRK2, the activity of βAR is increased and the metabolic rate is increased.

The concept of a metabolic regulator comes from an animal model of nutritional DM. Psaznomys obesus, a desert gerbil that survives on a low energy diet, develops insulin resistance and type 2 DM when placed on a high energy diet. As shown herein, diabetes is corrected when GRK2 activity is inhibited, thereby supporting the concept that manipulation of a metabolic rheostat is a treatment for DM.

The following information further substantiates the concept of such a metabolic rheostat: Up-regulation of GRK also causes decreased βAR in the heart which exacerbates heart failure. Inhibition of GAST by an inhibitor delivered locally to the heart may improve its function. High GRK2 levels are associated with hypertension. GRK2 has a role in insulin secretion. GRK has a role in CNS signaling. GRK has a role in hormone secretion. GRK has a role in olfaction.

Any modulator of GAST will thus serve to change the level of GRK-associated signal transduction and thus will act modulate a metabolic parameters.

Small Molecule Inhibitors

Low molecular weight organic molecules can act as inhibitors of GRK directly by binding to the kinase and by this inhibit the GAST. Such low molecular weight organic molecules are known in the art. Preferred low molecular weight organic molecules are GRK2 inhibitor H8, tri-fluorperazine, polyanions such as heparin and dextran sulfates.

Ribozymes that Specifically Cleave GRK—RNA

A specific modulator of GAST is a ribozyme that is a catalytic oligonucleotide (typically RNA). The catalytic nucleotide can be tailored to specifically recognize, via hybridization, a specific mRNA region and thus cleave it and eliminate its expression. The ribozymes may be introduced to the cell as catalytic RNA molecules or as expression constructs for the expression of the catalytic RNA molecules.

Antisense GAST Inhibitors

Another type of inhibitor of GAST is anti-sense nucleic acids. The nucleic acids are single stranded ribonucleic or deoxyribonucleic acid strands which contain nucleotides joined together through normal sugar-phosphate bonds. Antisense sequences can inhibit production of GRK protein by one of three mechanisms. By a first mechanism these antisense interfere with transcription as these antisense hybridize within the structural gene or in the regulatory region of the gene that encodes for GRK. This hybridization interrupts the transcription of GRK gene into mRNA. Since proper transcription or expression is effectively blocked by the hybridization of the anti-sense nucleic acids to the DNA, the kinase production is decreased and as a result of the depletion of the kinase the GAST is inhibited.

A second mechanism is the binding of the antisense in the cytoplasm to the mRNA, thus interfering with the formation of a proper translation construct leading to inhibition of translation of the mRNA to the protein. This leads to the decrease in the amount of GRK protein produced and thus to an inhibition of GAST.

A third mechanism is the formation of an mRNA-antisense duplex which leads to rapid degradation of mRNA duplex by RNases (such as RNase H). All these mechanisms lead to production of smaller amounts of GRK produced by the cells than without the presence of these anti-sense nucleic acids, thus leading to GAST inhibition.

The particular nucleotides that are joined together to form the anti-sense sequence are those that are complementary to a region of the GRK structural gene, or complementary to regulatory region of the gene sufficient to inhibit production of functional GRK. These nucleotides of the anti-sense nucleic acids are specifically determined by the nucleotides of the target location and can easily be identified by the skilled practitioner once the sequence of the target location is established. The target location is a matter of choice to some extent. It lies within the region of the structural gene that encodes GRK or in the regulatory coding region of the structure. The target location nucleotide sequence can easily be established by the skilled practitioner from publicly available information concerning the GRK gene or can be obtained by routine examination of homologous genes coupled with standard molecular biology techniques.

By one option, the antisense is an oligonucleotide of several to several tens of nucleotides that are inserted into the cells. This is the preferred oligonucleotide in accordance with the invention. Typically the sequence is the first 20–25 nucleotides in the 5' terminal of the GRK cDNA (that are complementary to the mRNA) An example of such sequence is:

for GRK2 is: ctcggcctcg ggcgcggccg agcgccgcgc (SEQ ID NO:39)

and for GRK3 is: caagcttcat ctgtatttac agctgctcgc (SEQ ID NO:40)

or the RNA version of the above where T has been replaced by U.

Another option is the use of longer antisense sequences (up to several hundred nucleotides) by insertion into an expression vector, which can then be transfected into cells by various gene transfer technologies. In that case, the full sequence of the GRK can be used to construct a sequence which is complementary to it to produce a long antisense rnRNA complementary to the native RNA. Finding the target of the kinase sequence to be used for antisense purposes may be carried out by screening through various overlapping sequences, or by use of various bio informative software that can locate likely targets in a given gene and give several alternative sequences for producing antisense sequences that can eliminate production.

Negative Dominant Kinase Genes

Still another type of inhibitor of GAST is negative dominant GRK genes. The presence of these genes in cells allows non-finctional GRK to be expressed to the exclusion of functional GRK. The negative dominant in the cells is inhibitory of GAST activity because this kinase is non-functional. Non-functional kinases, by definition, have no kinase activity. Negative dominant GRK genes are introduced into the cells by gene transfer techniques, which are becoming increasingly more standard in the art (calcium precipitation, electrical discharge, physical injection, use of carriers such as recombinant vectors, etc.). The introduced negative dominant GRK gene is incorporated in the cell's genome. There, copies of it are passed to progeny cells. Since this GRK- gene is negative dominant, it will be expressed in response to signals which induce GRK expression rather than the active form of GRK. Cells which have incorporated the negative dominant GRK gene will not be able to desensitize GPCR at the same levels as control because the expressed GRK is inactive. The negative dominant GRK genes can be found in the art or can be produced by standard gene mutation techniques which are well known to skilled practitioners in the art. These genes can be suitably packaged for transgenic procedures by appropriate methods and materials known to the skilled practitioners.

An example of a construct for dominant-negative GRK2 is expression vector pEF-GRK2-K220W (phannci.org/scientificjournals/pharnaci/journal/2.htlm).

Another example of dominant-negative GRK are sequences coding for GRK wherein the codon for Lyn pr Lys which binds ATP in the catalytic unit, is replaced by codons coding for Ala or Met.

Antibodies Against GRK for Inhibitor GAST

A further type of inhibitors of GAST is antibodies that are immunoreactive with GRK. These antibodies bind to the kinase and thereby severely limit or prohibit its kinase activity or interrupt its interaction with other cellular components, all the above leading to GAST inhibition. The antibodies can be of any class or type. The binding site of the antibodies can be anywhere on the GRK molecule provided the immunoreactive binding between the antibody and the kinase molecule results in a severe inhibition of GAST. The antibodies can be polyclonal or monoclonal and are produced by techniques well-known to the skilled practitioner by using the GRK or immunogenic fragments thereof as the antigenic stimulus. The antibodies can be delivered to the individual by depositing suitable clonal cells which produce the antibodies, into the individual whose metabolism is to be modulated. These clonal cells secrete the antibodies into the bloodstream where they are carried to the target cancer cells for immunoreaction with the GRK proteins. Binding fragments of antibodies are also suitable provided they bind GRK with sufficient affinity so that the activity of the kinase is at least severely limited. Alternatively, the antibodies or suitable binding fragments can be introduced into the individual by any of a variety of techniques known to the skilled practitioner (physical injection, attachment to carriers that cross cell membranes, transgenic introduction into the prostate cancer cells for subsequent induction of expression, etc.). The secreted, introduced or expressed antibodies or suitable antibody fragments thereof immunoreactively bind to the GRK, thereby inhibiting their activity and thus GAST activity. Commercially available anti-GRK antibodies are available.

Compounds Comprising GRK Derived Peptides:

A further type of inhibitor of GAST is compounds comprising peptides, which herein are designated as "GRK-derived peptides". These compounds comprising or consisting of said GRK-derived peptides are the preferred inhibitors of GAST in accordance with the invention, and thus are the preferred agents for the modulation of a metabolic parameter and for the treatment of metabolic associated conditions. The peptides apparently mimic a region in the kinase and thus bind to other cellular components with which the GRK interacts (such as the kinase substrates GPCRs) . This binding interrupts the kinase-component interaction (especially kinase-substrate interaction) and thus inhibit GAST.

This GAST modulation leads to change in the desensitizing activity of GPCR by GRK -leading to modulation of metabolism.

The peptides according to the above non-limiting theory, mimic a region in the GRK kinase which is involved in the interaction of the GRK with other cellular components which are part of the GRK-associated signal transduction. Preferably, these cellular components are selected from: the substrates of GRK, other kinases, phosphatases, as well as co-factors and ATP. Thus, any peptide which mimics a part of the GRK responsible for said interaction can bind to the cellular component, and thus inhibit the GAST.

Specific preferred regions of the GRK that the GRK-derived peptides mimic are the HJ-loop, αD-loop, A-region, and B4–B5 region, as defined above, most preferably the region mimicked is the HJ-loop.

It is clear that for interruption of the kinase-cellular component interaction, there is no need to obtain a mimic of the full specific region of the kinase and a mimic of a subsequence that binds to the substrate in a competitor may be sufficient to interrupt said interaction, for example, by steric hindrance. It is further clear that the interruption may be caused by mimicking of any one of several smaller subsequences present in the region so that there can be several alternative subsequences. It is further clear that for mimicking purposes it is not necessary to obtain a sequence identical to the one present in the native kinase and variants of that sequence, that can faithfully copy the overall three dimensional structure of the region (when present in the full kinase) as well as the chemical characteristics of those side chains involved with interaction to the substrate, can also be used as mimics for interruption of the interaction. At times such variants may have better mimicking properties than the native sequence, as the variation may help stabilize the mimic amino acid sequence in a more favorable conformation, or may have stronger binding properties to the substrate.

The peptide derivatives are short subsequences of at least five continuous amino acids obtained from the above sequences, as well as variants of the above sequences obtained by substitution of up to 40% of the amino acid with natural and non-natural amino acids or with peptidomimetic moieties, and/or variants obtained by chemical modification of up to 40% of the amino acids, and/or deletions of up to 20% of the amino acids, provided that at least 50% of the amino acids are identical to the sequence of the parent protein, and provided that the variant maintains the biological properties of the parent sequence.

Most preferably, the sequence is at least five continuous amino acids obtained from the region of positions 382 to 414 HJ-loop, more preferably from positions 383 to 396 in said HJ-loop. The amino acid sequence may be a sequence of 5, 6, 7, 8, 9, 10, 11, 12, 13, 14, 15, 16, 17, 18, 19 or 20 amino acids. The sequence may be a sequence that is naturally appearing in the HJ-loop. However, actual empirical experiments show that sequences having substitutions at times have better GAST inhibiting properties than native sequences. Therefore, in the scope of the present invention are also included variants of the native sequence of the at least five continuous amino acids from the HJ-loop, in which up to 40% of the amino acids have been substituted, up to 40% of the amino acids have been chemically modified, and/or up to 20% have been deleted, provided that the variant shows at least 50% of its amino acid with the native sequence. In general, amino acids in the regions, and in particular the HJ-loop region, which are essential for GAST, should be either identical to those appearing in the native sequence, should be chemically modified or alternatively, should contain conservative substitutions (in the context of the present invention conservative substitutions also refer to substitutions by amino acids having the same steric properties, but when the replaced amino acid is charged, the substituted amino acid may be polar or hydrophobic as well). The other positions in the sequence may be replaced by conservative, or non-conservative substitutions, both by naturally and non-naturally occurring amino acids, as well as by organic peptidomimetics, or these positions may be deleted or chemically modified.

In this invention, particularly preferred peptides for inhibition of GAST are K024H001 (SEQ ID NO.: 1), K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H108 (SEQ ID NO.: 11), K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), as well as compounds comprising any one of SEQ ID NO:20 to SEQ ID NO:38 associated with a moiety for transport across cellular membranes.

1. Addition of Non-peptidic Group to One or to Both of the Terminals of the GRK-derived Peptides Where the compound of the invention is a linear molecule, it is possible to place in any of its terminals various functional groups. The purpose of such a functional group may be for the improvement of the GAST inhibition. The functional groups may also serve for the purpose of improving physiological properties of the compound not related directly to GAST inhibition such as: improvement in stability, penetration (through cellular membranes or barriers), tissue localization, efficacy, decreased clearance, decreased toxicity, improved selectivity, improved resistance to repletion by cellular pumps, and the like. The functional groups may be also detectable labels added for diagnostic or research purposes. For convenience sake the free N-terminal of one of the sequences contained in the compounds of the invention will be termed as the N-terminal of the compound, and the free C-terminal of the sequence will be considered as the C-terminal of the compound (these terms being used for convenience sake). Either the C-terminus or the N-terminus of the sequences, or both, can be linked to a carboxylic acid functional groups or an amine functional group, respectively.

Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds, these being a specific preferred example for "a moiety for transport across cellular membranes".

These moieties can be cleaved in vivo, either by hydrolysis or enzymatically, inside the cell. (Ditter et al., *J. Pharm. Sci.* 57:783 (1968); Ditter et al., J. Pharm. Sci. 57:828 (1968); Ditter et al., J. Pharm. Sci. 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., Arch. Biochem. Biophys. 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a compound of the present invention is protected, preferably with a methyl, ethyl, benzyl or substituted benzyl ester, more preferably as a benzyl ester.

In addition, a modified lysine residue can be added to the C-terminal of the compound to enhance biological activity. Examples of lysine modification include the addition of an aromatic substitute, such as benzoyl benzoic acid, dansyl-lysine various derivatives of benzoic acids (difluoro-, tri-fluromethy-, acetamido-, dimethyl-, dimethylamino-, methoxy-) or various derivatives of carboxylic acid (pyrazine-, thiophene-, pyridine-, indole-, naphthalene-, biphenyl,), or an aliphatic group, such as acyl, or a myristic or stearic acid, at the epsilon amino group of the lysine residue.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)—CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO—and (substituted benzyl)-CO—. Examples of alkoxy carbonyl and aryloxy carbonyl groups include CH3—O—CO—, (ethyl)-O—CO—, n-propyl—O—CO—, iso-propyl-O—CO—, n-butyl-O—CO—, sec-butyl-O—CO—, t-butyl-O—CO—, phenyl-O—CO—, substituted phenyl-O—CO—and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —$NH_2$, —$NHR_2$ and —$NR_2R_3$) or ester (i.e. the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0–2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl) (ethyl), —NH(benzyl), —N(C1–C4 alkyl) (benzyl), —NH(phenyl), —N(C1–C4 alkyl) (phenyl), —$OCH_3$, —O—(ethyl), —O—(n-propyl), —O-(n-butyl), —O-(iso-propyl), -O-(sec-butyl), —O-(t-butyl), —O-benzyl and –O-phenyl.

Preferably the compounds includes in the N-terminal a hydrocarbon having a length of $C_4$–$C_{20}$ preferably $C_6$–$C_{18}$, most preferably $C_8$–$C_{16}$. Example of hydrophobic moieties are: aaystyl, stearyl, lauroyl, palmitoyl and acetyl etc.

2. Finding Shorter Subsequences of GRK-derived Peptides

As indicated, GRK-derived peptides included in the compounds for inhibition of GAST, are obtained by finding which sequences from the above regions (HJ-loop, A-region, αD-region, B4–B5 region) inhibit GAST. Typically it is desired, for ease of synthesis and administration, to find the shortest sequence possible which is still active. In the following, the finding of the shortest sequence will be disclosed in connection with the HJ-loop, but this description is applicable also to the other regions.

A shorter subsequence of the HJ-loop comprising a continuous stretch of at least five amino acid can be found by preparing a series of partially overlapping peptides each of 5–10 amino acids and each obtained by synthesizing a sequence that is one position removed from the previous sequence.

For example, the HJ-loop is in position 382–414. If it is to be desired to prepare 10 aa peptides, then the following, partially overlapping peptides are prepared: a peptide having the sequence 382–391, 383–392, 384–393, . . . 405–414. The GAST inhibiting activities of the subsequences is then determined in a test assay. The best 10-aa peptide is then chosen.

For checking whether the 10 aa peptide can be reduced in sequence, it is possible to either repeat the above procedure (preparing a series of partially overlapping peptides) using 5 aa long peptides that span the length of the chosen 10 aa peptide, or to shorten the 10 aa peptide by deleting alternatively from each terminal, an amino acid, and testing the GAST inhibiting activity of the progressively truncated peptides, until the optimal sequence of at least 5, at least 6, at least 7, at least 8, or at least 9 aa peptide is obtained or until it is determined that longer sequences are required. As the HJ-loop (as well as the other regions) is relatively small, typically the number of different peptides to be tested is also small. For example, for an HJ-loop having a length of about 20 aa, there is a need to prepare only 12 peptides to find the optimal 8 aa peptide. After the best 8-aa peptide is obtained, it is possible to delete sequentially amino acids from one or both terminals of the 8 mer peptide for obtaining the shortest sequence of 5, 6 or 7 aa that is still active. For these steps only 16 sequences have to be tested, so that by testing only 24 peptides it is possible to find such a shorter sequence.

3. Identifying Essential and Non-essential Amino Acids in the Subsequence Chosen A. Ala-Scan Once the shorter continuous stretch of at least 5 (at least 6, 7, 8, 9, 10, 11, 12 or 13) amino acids has been identified, as explained above, it is necessary to realize which of the amino acids in the stretch are essential (i.e. crucial for the kinase-associated signal transduction modulation) and which are non-essential. Without wishing to be bound by theory, in almost every native protein involved in interaction with other cellular components, some amino acids are involved with the interaction (essential amino acids) and some amino acids are not involved in the interaction (non-essential amino acids), for example since they are cryptic and inaccessible. A short peptide which is to mimic a region of the GRK protein behaves in the same way as the region when present in the full kinase: some amino acids actually interact with the substrate (or other interacting components) and other amino acids merely serve to spatially position the interacting amino acids, but do not participate in the interaction with the other cellular components.

Essential amino acids have to be maintained (i.e. be identical to those appearing in the native kinase), or replaced by conservative substitutions (see definition below) to obtain variants of the peptides or can be chemically modified. Non-essential amino acids can be maintained, deleted, chemically modified, replaced by a spacer or replaced by conservative or non-conservative substitutions.

Identification of essential vs. non-essential amino acids in the peptide can be achieved by preparing several peptides that have a shorter sequence than the full region (see 2 above) in which each amino acid is sequentially replaced by the amino acid Ala ("Ala-Scan."), or sequentially each amino acid is omitted ("omission-scan"). This allows to identify the amino acids which modulating activity is decreased by said replacement/omission ("essential") and which are not decreased by said replacement/omission ("non-essential") (Morrison et al., *Chemical Biology* 5:302–307, 2001). Another option for testing the importance of various peptides is by the use of site-directed mutagenesis. Other Structure-Activity-Relationship (SAR) techniques may also be used.

B. 3-D Analysis

Another strategy for finding essential vs. non-essential amino acids is by determining which aa of the A-region, in the 3D of the full kinase are exposed and which are cryptic.

Typically cryptic aa are non-essential and exposed or partially exposed are more likely to be essential. However, if one wishing to "guess" theoretically which "non-conservative" substitutions in the cryptic region can be tolerated, a good guideline is to "check" on a 3D computer model of the full kinase, whether these changes drastically alter the overall shape of the regions when the "altered" peptide is superimposed on the full kinase. Those non-conservative substitutions, that when simulated on a computer 3D structure (for example using the Triphose™ software) do not cause drastic alterations of the overall shape of the regions (drastic shifting in the positions of the exposed amino acids) are likely non-conservative replacements. Thus prior to experimental testing it is possible to reduce the number of tested candidates by computer simulation. Where the 3D structure of a specific kinase is not available in actual crystallography data, it is possible to obtain a "virtual" 3D structure of the kinase based on homology to known crystallographic structures using such progress such as CompSer™ (Tripose, USA).

4. Obtaining Variants

The sequence regions of the compound of the invention may be the native sequences obtained from the GRK (preferably the shortest possible sequence from the region that has the highest activity), or alternatively variants of the native sequence obtained by deletion, (of non-essential amino acids) or substitution (only conservative substitutions in essential positions, both conservative and non-conservative of non-essential acids) or chemical modifications.

4.1 Deletions and Insertions

Deletions can occur in particular of the "non-essential amino acids". Additions may occur in particular at the N-terminal or the C-terminal of any of the amino acids of the sequence. No more than 20%, preferably 10% most preferably none of the amino acids should be deleted. Insertions should preferably be N-terminal or C-terminal to the sequence of (a) to (g) or between the several sequences linked to each other in (i). However other insertions or deletions are possible. Again, the putative effect of the deletions on the mimicking properties of the peptides can be evaluated virtually by reverting to the 3D-module as described above.

4.2 Replacements/Substitutions

The variants can be obtained by replacement (termed also in the text as "substitution") of any of the amino acids as present in the native kinase. As may be appreciated there are positions in the sequence that are more tolerant to substitutions than others, and in fact some substitutions may improve the activity of the native sequence. The determination of the positions may be realized using "Ala-Scan," "omission scan" "site directed mutagenesis" or 3-D theoretical considerations as described in 3 above. Generally speaking the amino acids which were found to be "essential" should either be identical to the amino acids present in the native specific kinase or alternatively substituted by "conservative substitutions" (see bellow). The amino acids which were found to be "non-essential" might be identical to those in the native peptide, may be substituted by conservative or non-conservative substitutions, and may be deleted or replaced by a "spacers".

The term "naturally occurring amino acid" refers to a moiety found within a peptide and is represented by —NH—CHR—CO—, wherein R is the side chain of a naturally occurring amino acid.

The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well-known in the art; a large number of these analogs are commercially available. Many times the use of non-naturally occurring amino acids in the peptide has the advantage that the peptide is more resistant to degradation by enzymes which fail to recognize them.

The term "conservative substitution" in the context of the present invention refers to the replacement of an amino acid present in the native sequence in the specific kinase with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the native amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound.

For example in accordance with the invention the following substitutions are considered as conservative: replacement of arginine by cytroline; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid would have the same or a similar functional group in the side chain as the original amino acid.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, $—CH_2CH_2OH$, $—CH_2CH_2CH_2OH$, $—CH_2CHOHCH_3$ and $—CH_2SCH_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginine, N-nitroarginine, β-cycloarginine, μ-hydroxyarginine, N-amidinocitruline and 2-amino-4-guanidinobutanoic acid, homologs of lysine, homologs of arginine and omithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1–C5 straight or branched alkyl side chains substituted with —OH or —SH. Preferably, Group VI includes serine, cysteine or threonine.

In this invention any cysteine in the original sequence or subsequence can be replaced by a homocysteine or other sulfhydryl-containing amino acid residue or analog. Such analogs include lysine or beta amino alanine, to which a cysteine residue is attached through the secondary amine yielding lysine-epsilon amino cysteine or alanine-beta amino cysteine, respectively.

The term "non-conservative substitutions" concerns replacement of the amino acid as present in the native GRK by another naturally or non-naturally occurring amino acid, having different electrochemical and/or steric properties, for example as determined by the fact the replacing amino acid is not in the same group as the replaced amino acid of the native kinase sequence. Those non-conservative substitutions which fall under the scope of the present invention are those which still constitute a compound having GRK-associated signal transduction modulating activities. Because D-amino acids have hydrogen at a position identical to the glycine hydrogen side-chain, D-amino acids or their analogs can often be substituted for glycine residues, and are a preferred non-conservative substitution. In particular, preferred are replacements of Gly by D-Lys or D-Arg.

A "non-conservative substitution" is a substitution in which the substituting amino acid (naturally occurring or modified) has significantly different size, configuration and/or electronic properties compared with the amino acid being substituted. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NE—CH [(—$CH_2)_5$—COOH]—CO—for aspartic acid.

Alternatively, a functional group may be added to the side chain, deleted from the side chain or exchanged with another functional group. Examples of non-conservative substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or omithine. In yet another alternative, the side chain of the substituting amino acid can have significantly different steric and electronic properties from the functional group of the amino acid being substituted. Examples of such modifications include tryptophan for glycine, lysine for aspartic acid and —$(CH_2)_4$COOH for the side chain of serine. These examples are not meant to be limiting.

As indicated above the non-conservative substitutions should be of the "non-essential" amino acids.

Preferably, the GRK may be substituted by benzylamine groups, by biotinylation. Another substitution is di-iodinization of tyrosine. Gly-residue may be substituted by D-isomers especially D-Lys residues.

"Peptidomimetic organic moiety" can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the compounds retain their tissue-remodeling modulating activity as compared to compounds constituting sequence regions identical to those appearing in the native kinase.

Peptidomimetics are often used to inhibit degradation of the peptides by enzymatic or other degradative processes. The peptidomimetics can be produced by organic synthetic techniques. Examples of suitable peptidomimetics include D amino acids of the corresponding L amino acids, tetrazol (Zabrocki et al., *J. Am. Chem. Soc.* 110:5875–5880 (1988)); isosteres of amide bonds (Jones et al., Tetrahedron Lett. 29: 3853–3856 (1988));

LL-3-amino-2-propenidone-6-carboxylic acid (LL-Acp) (Kemp et al., *J. Org. Chem.* 50:5834–5838 (1985)). Similar analogs are shown in Kemp et al., Tetrahedron Lett. 29:5081–5082 (1988) as well as Kemp et al, Tetrahedron Lett. 29:5057–5060 (1988), Kemp et al., Tetrahedron Lett. 29:4935–4938 (1988) and Kemp et al, *J. Org. Chem.* 54:109–115 (1987). Other suitable peptidomimetics are shown in Nagai and Sato, Tetrahedron Lett. 26:647–650 (1985); Di Maio et al., *J. Chem. Soc. Perkin Trans.*, 1687 (1985); Kahn et al., Tetrahedron Lett. 30:2317 (1989); Olson et al., *J. Am. Chem. Soc.* 112:323–333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53–76 (1989)); 1,2,3,4-tetrahydro-isoquinoline-3-carboxylate (Kazmierski et al., *J. Am. Chem. Soc.* 133:2275–2283 (1991)); histidine isoquinolone carboxylic acid (HIC) (Zechel et al., *Int. J. Pep. Protein Res.* 43 (1991)); (2S, 3S)-methylphenylalanine, (2S, 3R)-methyl-phenylalanine, (2R, 3S)-methyl-phenylalanine and (2R, 3R)-methyl-phenylalanine (Kazmierski and Hruby, Tetrahedron Lett. (1991)). Another example of a peptidomimetic (peptidioid) is a moiety wherein the N- of the peptidic backbone has been modified by an addition of a methyl substituent.

4.3 Chemical Modifications

This term refers to the modification of an existing amino acid residue of the native sequence by the same residue bearing functional groups. Such "chemical modifications" may take place in the process of GRK-synthesis of the molecule, i.e. during elongation of the amino acid chain chemical modification is introduced by adding an a priori modified amino acid. However, chemical modification of an amino acid can also take place when the residue is present in the molecule or sequence ("in situ" modification).

The amino acid of any of the sequence regions of the molecule can be 5 chemically modified by carboxymethylation, acylation, phosphorylation, glycosylation or fatty acylation. Ether bonds can be used to join the serine or threonine hydroxyl to the hydroxyl of a sugar. Amide bonds can be used to join the glutamate or aspartate carboxyl groups to an amino group on a sugar. The C-terminal amino acid may be acylated, modified by addition of hydroxy amidate. (Garg and Jeanloz, Advances in *Carbohydrate Chemistry and Biochemistry*, Vol. 43, Academic Press (1985); Kunz, *Ang. Chem. Int.* Ed. English 26:294–308 (1987)). Acetal and ketal bonds can also be formed between amino acids and carbohydrates. Fatty acid acyl derivatives can be made, for example, by free amino group (e.g., lysine) acylation (Toth et al., Peptides: Chemistry, *Structure and Biology*, Rivier and Marshal, eds., ESCOM Publ., Leiden, 1078–1079 (1990)).

Other examples are addition of iodo groups to the residues for radio-imaging purposes.

4.4 Cyclization of the Molecule

The present invention also includes cyclic compounds which are cyclic molecules.

A "cyclic molecule" refers, in one instance, to a compound of the invention in which a ring is formed by the formation of a peptide bond between the nitrogen atom at the N-terminus and the carbonyl carbon at the C-terminus.

"Cyclized" also refers to the forming of a ring by a covalent bond between the nitrogen at the N-terminus of the compound and the side chain of a suitable amino acid in the sequence present therein, preferably the side chain of the C-terminal amino acid. For example, an amide can be formed between the nitrogen atom at the N-terminus and the carbonyl carbon in the side chain of an aspartic acid or a glutamic acid. Alternatively, the compound can be cyclized by forming a covalent bond between the carbonyl at the C-terminus of the compound and the side chain of a suitable amino acid in the sequence contained therein, preferably the side chain of the N-terminal amino acid. For example, an amide can be formed between the carbonyl carbon at the C-terminus and the amino nitrogen atom in the side chain of a lysine or an ornithine. Additionally, the compound can be cyclized by forming an ester between the carbonyl carbon at the C-terminus and the hydroxyl oxygen atom in the side chain of a serine or a threonine.

"Cyclized" also refers to forming a ring by a covalent bond between the side chains of two suitable amino acids in the sequence present in the compound, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in the side chain of, for example, a lysine or an ornithine.

In addition, a compound can be cyclized with a linking group between the two termini, between one terminus and the side chain of an amino acid in the compound, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAl) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd and Acm is easily removed by iodine treatment.

5. Pharmaceutical Compositions and Therapeutical Methods of Treatment

The inhibitor of GAST of the present invention, or the compounds comprising the GRK-derived peptides can be used as active ingredients (together with a pharmaceutically acceptable carrier) to produce a pharmaceutical composition. The pharmaceutical composition may comprise one, or a mixture of two or more of the different GAST inhibitors of the invention in an acceptable carrier.

The pharmaceutical composition should be used for the treatment of any disease, disorder, or condition, wherein a beneficial therapeutical effect may be evident by the modulation of at least one metabolic parameter, especially for the treatment of a disease selected from diabetes, obesity, dislipidemia, hypertension, syndrome-X associated phenomena.

The GAST modulators of the present invention can be administered parenterally. Parenteral administration can include, for example, systemic administration, such as by intramuscular, intravenous, subcutaneous, or intraperitoneal injection. Compounds which resist proteolysis can be administered orally, for example, in capsules, suspensions or tablets. The compound can also be administered by inhalation or insufflations or via a nasal spray.

The GAST inhibitors can be administered to the individual in conjunction with an acceptable pharmaceutical carrier as part of a pharmaceutical composition for treating the diseases discussed above. Suitable pharmaceutical carriers may contain inert ingredients which do not interact with the compounds. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al, *Controlled Release of Biological Active Agents*, John Wiley and Sons, 1986). The formation may be also resources for administration to skin, or in the form of salve, solution, ointment, etc. for topical administration.

The composition may be administered locally to the site of activity such as administered directly into the heart.

The pharmaceutical compositions may also be administered in conjunction with other modes of metabolic therapy, for example, with other compounds used to treat metabolic diseases, such as insulin, as it may work synergistically with insulin and this decrease the amount of insulin required, or decrease the frequency of insulin administration.

A "therapeutically effective amount" is the quantity of compound which results in an improved clinical outcome as a result of the treatment compared with a typical clinical outcome in the absence of the treatment. An "improved clinical outcome" results in the individual with the disease experiencing fewer symptoms or complications of the disease, including a longer life expectancy, as a result of the treatment. With respect to diabetes, an "improved clinical outcome" refers to decreased blood glucose levels, improved responses to insulin, starvation, stress, or glucose load in the presence of the compound of the invention, a longer life expectancy, a reduction in the complications of the disease (e.g., neuropathy, retinopathy, nephropathy and degeneration of blood vessels associated with diabetes) and an improved quality of life, as described above. Another aspect of an improved clinical outcome is a reduction in medication dosage (e.g., a reduction in insulin or other hypoglycemic agent needed to maintain adequate blood glucose levels).

With respect to obesity, an improved clinical outcome refers to increased weight reduction per calorie intake. It also refers to a decrease in the complications which are a consequence of obesity, for example heart disease such as arteriosclerosis and high blood pressure. With respect to syndrome X an improved clinical outcome refers to a longer life expectancy, a reduction in the incidence or severity of the different mobilities included in the syndrome (e.g., ischemic heart disease, atherosclerosis, type II DM and obesity) and an improved quality of life. With respect to other manifestations of syndrome X, it includes lowering of blood pressure and improvement of serum lipid and cholesterol profile.

6. Determination of GAST Modulating Activity

It should be appreciated that some of the compounds that comprise sequences (a)–(i) above are better GAST modulators than others. Some of the conservative substitutions in the essential positions may diminish the modulating, while other such conservative substitution in the essential positions may improve these modulating activities. The same is true also for deletions, substitutions (both conservative and non-conservative) in non-essential positions, as well as to chemical modifications (in any position) or insertions. In addition the type and size of the non-amino acid portion of the compounds, such as a hydrophobic moiety in one of its terminals may diminish or increase the GAST modulating activities. The GAST modulating activities that can be determined for example by using one of the assays stipulated below.

6.1 Cellular Assays

It can be readily determined whether a compound modulates the activity of a GAST by incubating the compound with cells which have one or more cellular activities controlled by the GAST. Examples of these cellular activities include cell proliferation, cell differentiation, cell morphology, cell survival or apoptosis, cell response to external stimuli, gene expression, lipid metabolism, glycogen or glucose metabolism and mitosis, secretion or production of compounds by the cells. The cells are incubated with the candidate compound to produce a test mixture under conditions suitable for assessing the level of the GAST. The activity of the GAST is assessed and compared with a suitable control, e.g., the activity of the same cells incubated under the same conditions in the absence of the candidate compound (or in the presence of a control compound). A lesser activity of GAST in the test mixture compared with the control indicates that the candidate compound modulates GAST.

Suitable cells for the assay include normal cells which express the GRK-, cells which have been genetically engineered to express a GRK, malignant cells expressing a GRK or immortalized cells that express the kinase.

Conditions suitable for assessing activity include conditions suitable for assessing a cellular activity or function under control of the GAST pathway. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors or of specific activators such as cytokines, hormones and the like).

For example, the activity may be assessed by measuring melanogenesis by melanocytes as in Example 3 below. Another cellular assay is determination of cAMP in C6 glioblastoma cells as indicatedin example 4 bellow.

6.2 Phosphorylation of Substances

It is possible to assess the GAST activity and the changes in this GAST as compared to control, by determining the phosphorylation level of the substrate proteins of the GRK. Examples of possible GRK substrates are: tubuline, $\beta$-adrenergic receptor, $\alpha_2$adrenergic receptor, acetylcholine receptor, d-opioid-receptor and $\mu$-opioid-receptor as $\beta_{2/1}$-adrenergic receptor, $\alpha_2$-adrenergic receptor, acetylcholine receptor, d-opioid receptor, rhodopsin ,$A_{(1,2,3\,)}$—purinergic receptor, synuclein, Angiotensin II 1a, DA-dopamine, N-formyl peptide, muscarinic receptor, platelet activating factor, thrombin (Bunemann et al, *J. of Physiology* (1999) 517.1,5–23) Cells known to express the GRK such as for example are incubated with a candidate compound for inhibiting the GAST. Then the cells are lysed, the protein content of the cells is obtained and separated on a gel. The substrates can be identified by use of suitable molecular weight markers, or by using suitable antibodies, reactive against the specific GPCR used. The level of phosphorylation of the substrate may be determined by suing labeled anti-Tyr antibodies. Alternatively, the suitable substrate may be immuno-precipitated using antibodies. The level of substrate phosphorylation in the immuno-precipitate can be determined by using anti-phosphotyrosine antibodies (see Fujimoto et al., *Immunity,* 13:47–57 (2000)).

By another option, phosphorylation may be determined in a cell-free system by incubating a mixture comprising GRK, the substrate of the kinase (the suitable GPCR) and candidate molecules for inhibiting GAST in the presence of ATP under conditions enabling phosphorylation. The proteins are then subjected to gel separation, transferred to nitrocellulose where the substrate band is identified by antibody or molecular weight marker followed by immunoblotting by anti-phosphotyrosine antibody. Alternatively it is possible to use [γ-$^{32}$ P] ATP and quantify the amount of radioactivity incorporated in the substrate (See Fujimoto et al., *The J. of Immunol.* 7088–7094 (1999).

6.3. Tissue or in Vivo Assay

Suitable assays for determining inhibition of GAST can be by inducing diabetes in animals for example, by injection of streptozotoun that destroys some of the insulin secreting cells (as long as some insulin is maintained) or by using animal models which have a tendency to develop diabetes, obesity, high serum lipid profile, hypertension, either naturally (sand rat, ob/ob mice etc.) or through genetic engineering, and then determining the change of glucose level in the blood of the animal. Other examples are determination of change of weight of appetite in the treated animals.

7. Preparation of Antibodies

The GRK-derived peptides of the present invention can be useful in the preparation of specific antibodies against GRK. Suitable antibodies can be raised against a GRK peptide by conjugating the peptide to a suitable carrier, such as keyhole limpet hemocyanin or serum albumin; polyclonal and monoclonal antibody production can be performed using any suitable technique. A variety of methods have been described (see e.g., Kohler et al., *Nature,* 256:495–497 (1975) and *Eur. J. Immurnol.* 6:511–519 (1976); Milstein et al., Nature 266: 550–552 (1977); Koprowski et al., U.S. Pat. No. 4,172,124; Harlow, E. and D. Lane, 1988, *Antibodies*: A Laboratory Manual, (Cold Spring Harbor Laboratory: Cold Spring Harbor, N.Y.); Current Protocols In Molecular Biology, Vol. 2 (Supplement 27, Summer 1994), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

The antibodies can be used to determine if an intracellular GRK is present in the cytoplasm of the cell. A lysate of the cell is generated (for example, by treating the cells with sodium hydroxide (0.2 N) and sodium dodecyl sulfate (1%) or with a non-ionic detergent like NP-40, centrifugating and separating the supernatant from the pellet), and treated with anti-GRK peptide antibody specific for GRK. The lysate is then analyzed, for example, by Western blotting or immunoprecipitation for complexes between GRK and antibody. Anti-GRK peptide antibodies can be utilized for the study of the intracellular distribution (compartmentalization) of GRK under various physiological conditions via the application of conventional immunocytochemistry such as immunofluorescence, immunoperoxidase technique and immunoelectron microscopy, in conjunction with the specific anti-GRK peptide antibody.

Antibodies reactive with the GRK peptides are also useful to detect and/or quantitate the GRK in a sample, or to purify the GRK (e.g., by immunoaffinity purification).

The GRK-derived peptides of the present invention can also be used to identify ligands which interact with GRK and which inhibit the activity of GRK. For example, an affinity column can be prepared to which a GRK peptide is covalently attached, directly or via a linker. This column, in turn, can be utilized for the isolation and identification of specific ligands which bind the GRK peptide and which will also likely bind the GRK. The ligand can then be eluted from the column, characterized and tested for its ability to inhibit GRK function.

8. Preparation of the Compounds

Peptide sequences for producing any of the sequence of the compounds of the invention may be synthesized by solid phase peptide synthesis (e.g., t-BOC or F-MOC) method, by solution phase synthesis, or by other suitable techniques including combinations of the foregoing methods. The t-BOC and F-MOC methods, which are established and widely used, are described in Aarifield, *J. Am. Chem. Soc.,* 88:2149 (1963); Meienhofer, Hormonal Proteins and Peptides, C. H. Li, Ed., Academic Press, 1983, pp. 48–267; and Barany and Aarifield, in The Peptides, E. Gross and J. Meienhofer, Eds., Academic Press, New York, 1980, pp.3–285. Methods of solid phase peptide synthesis are described in Aarifield, R. B., *Science,* 232:341 (1986); Carpino, L. A. and Han, G. Y., *J. Org. Chem.,* 37:3404 (1972); and Gauspohl, H. et al., *Synthesis,* 5:315 (1992)). The teachings of these references are incorporated herein by reference.

As indicated above the compounds of the invention may be prepared utilizing various peptidic cyclizing techniques. Methods of cyclizing compounds having peptide sequences are described, for example, in Lobl et al., WO 92/00995, the teachings of which are incorporated herein by reference. Cyclized molecules can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAl) (for the carboxyl group in the side chain of glutamic acid or aspartic acid, for example), allyloxy carbonyl (Aloc) (for the amino nitrogen in the side chain of lysine or omithine, for example) or acetamidomethyl (Acm) (for the sulthydryl of cysteine) protecting groups. OAl and Aloc are easily removed by Pd and Acm is easily removed by iodine treatment.

Other modes of cyclization (beyond N- to C-terminal cyclization) may include: N- to backbone cyclization, C- to backbone cyclization, N- to side chain cyclization, C- to side chain cyclization, backbone to side chain cyclization, backbone to backbone cyclization and side chain to side chain cyclization.

EXAMPLE 1

Preparation of Compounds Comprising GRK-derived Peptides

The compounds of this invention can be synthesized utilizing a 430A Peptide Synthesizer from Applied Biosystems using F-Moc technology according to manufacturer's protocols. Other suitable methodologies for preparing peptides are known to person skilled in the art. See e.g., Merrifield, R. B., *Science,* 232: 341 (1986); Carpino, L. A., Han, G. Y., *J. Org. Chem.,* 37: 3404 (1972); Gauspohl, H., et al., *Synthesis,* 5: 315 (1992)). The teachings of which are incorporated herein by reference.

Rink Amide Resin [4(2',4' Dimethoxyphenyl-FMOC amino methyl) phenoxy resin] was used for the synthesis of C-amidated peptides. The alpha-amino group of the amino acid was protected by an FMOC group, which was removed at the beginning of each cycle by a weak base, 20% piperidine in N-methylpyrrolidone (NMP). After deprotection, the resin was washed with NMP to remove the piperidine. In situ activation of the amino acid derivative was performed by the FASTMOC Chemistry using HBTU (2(1-benzotriazolyl-1-yl)-1,1,3,3-tetramethyluronium) dissolved in HOBt (1-hydroxybenzotriazole) and DMF (dimethylformamide). The amino acid was dissolved in this solution with additional NMP. DIEA (diisopropylethylamine) was added to initiate activation. Alternatively, the activation method of DCC (dicycbohexylcarbodiimide) and HOBL was utilized to form an HOBt active ester. Coupling was performed in NMP. Following acetylation of the N-terminus (optional), TFA (trifluoroacetic acid) cleavage procedure of the peptide from the resin and the side chain protecting groups was applied using 0.75 g crystalline phenol; 0.25 ml EDT (1,2-ethandithiol); 0.5 ml thioanisoie; 0.5 ml D. I. $H_2O$; 10 ml TFA.

EXAMPLE 2

Type II Diabetes in Sand Rats (Psamomys)

Sand-rats (psamomys) which are genetically prone to develop Type II diabetes were used in this study. The genetically selected sand-rats, 3 to 6 months old, were fed an energy-rich diet (Weizmann HE) for about 3 to 10 days until they became diabetic, as judged by their elevated blood-glucose level (see R. Kalman et al., "The Efficiency of Sand Rat Metabolism is Responsible for Development of Obesity and Diabetes", *J. of Basic & Clinical Physiology & Pharmacology* (1993), vol. 4, no. 1–2, pp 57–68, the pertinent portions of which are incorporated herein by reference).

The diabetic sand-rats were injected i.p. once a week with a compound comprising GRK-derived peptide K024H107 (SEQ ID NO:10) at a dose of 10 mg/kg. The peptide was prepared by diluting a 10 mM solution of the peptide in 100% DMSO with phosphate buffered saline (PBS) containing 0.1% bovine serum albumin (BSA) to a concentration of 400 μM. Forty μM of the 10 mM peptide in DMSO solution was mixed with 160 μl of 1.6M $NH_4HCO_3$ and heated for 40 minutes at 100° C. The resultant solution was then diluted to 400 μM in 2 M Hepes buffer (pH 7.0). This peptide stock solution was labeled "tbi". The vehicle of the solution for injection included 8% DMSO, 0.67M ammonium bicarbonate, and 2M Hepes. Control animals received an i.p. injection of the vehicle only. The results for treated animals are shown in FIG. 3, and for control animals are shown in FIG. 4.

Figure 4:
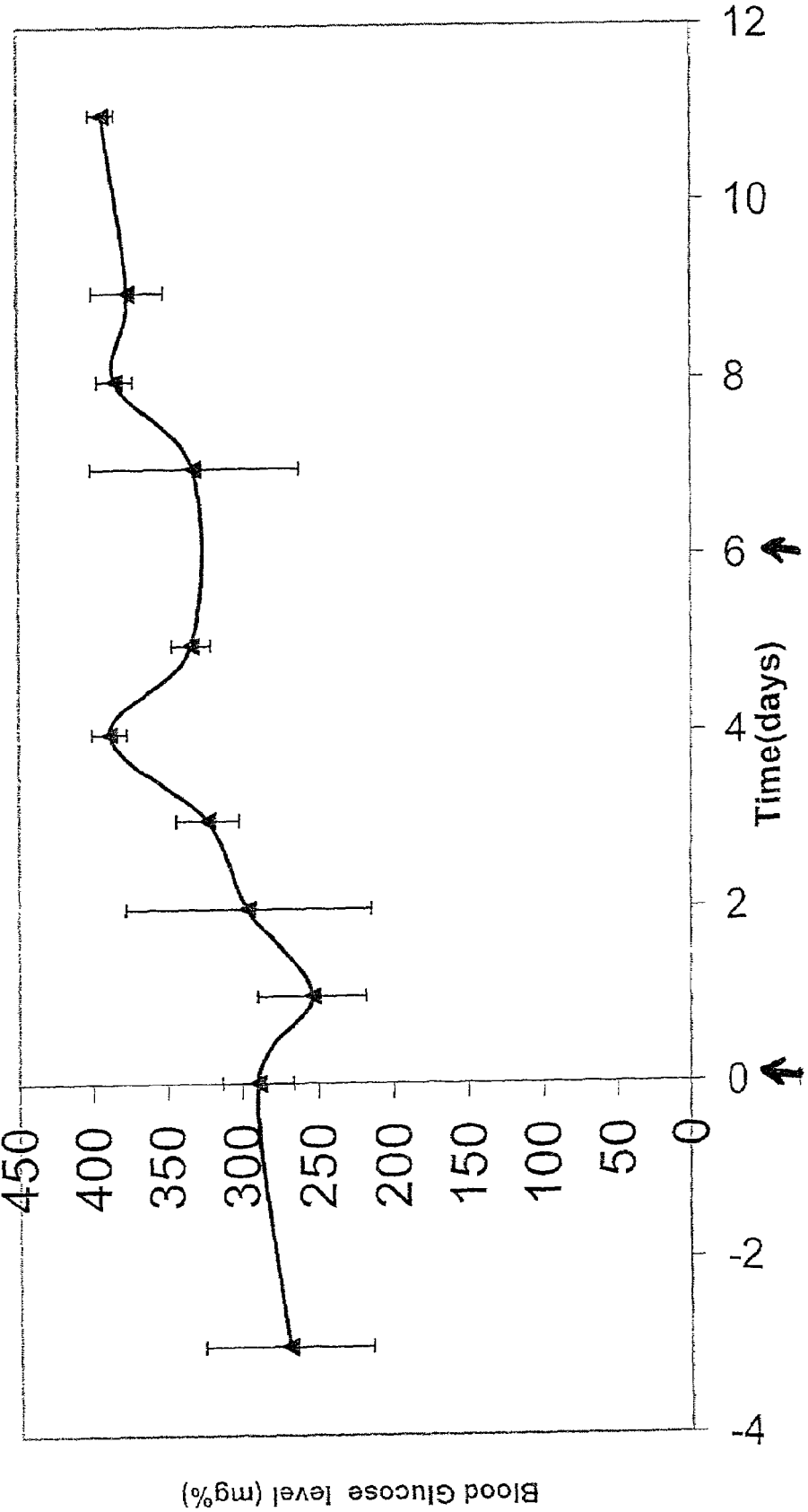
FIG. 4 is a graph that shows blood-glucose of control untreated sand rats (*psamomys obesus*).
Figure 5A:
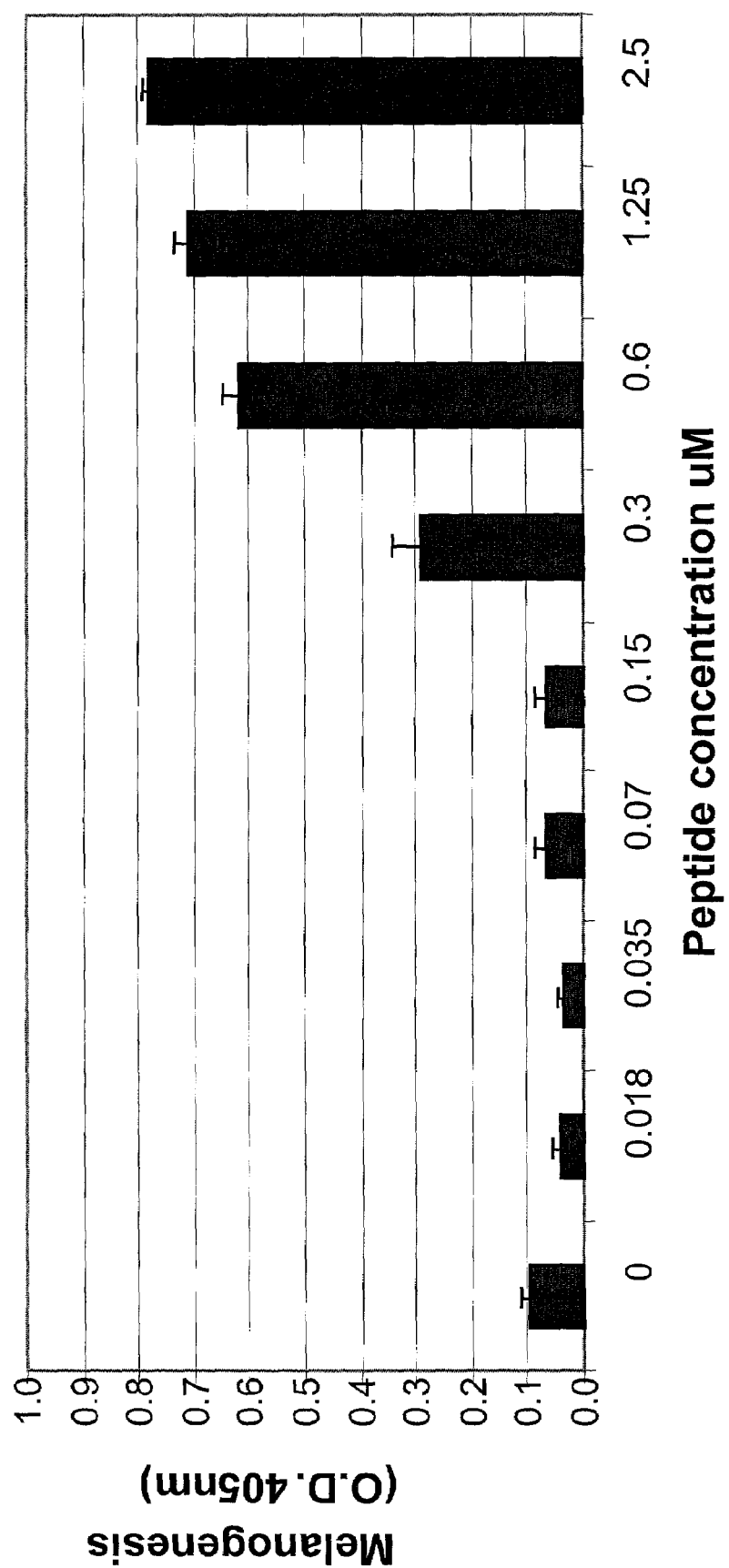
FIGS. 5A–5G are graphs illustrating the effects of peptides of the invention on melanogenesis by murine B16 melanoma cells.
Figure 5B:
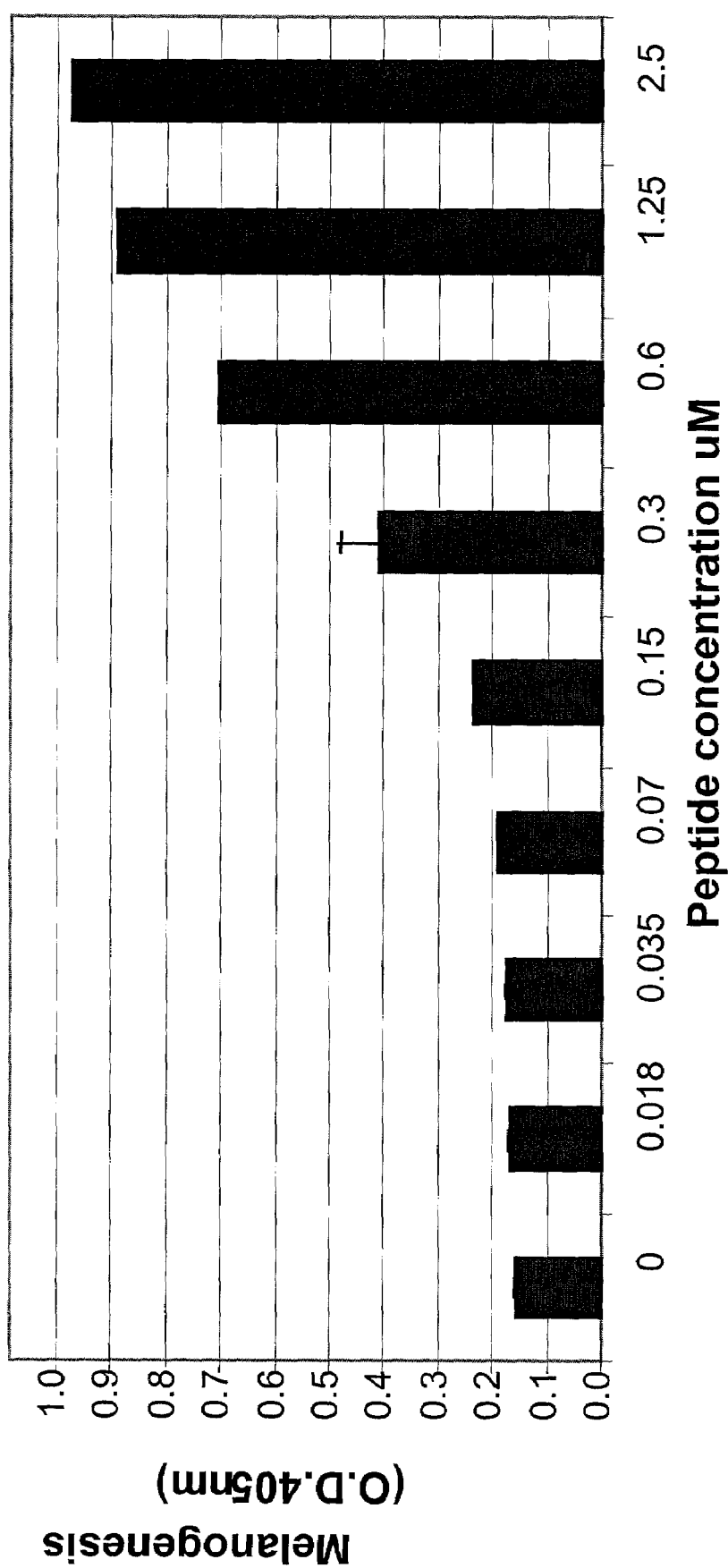
Figure 5C:
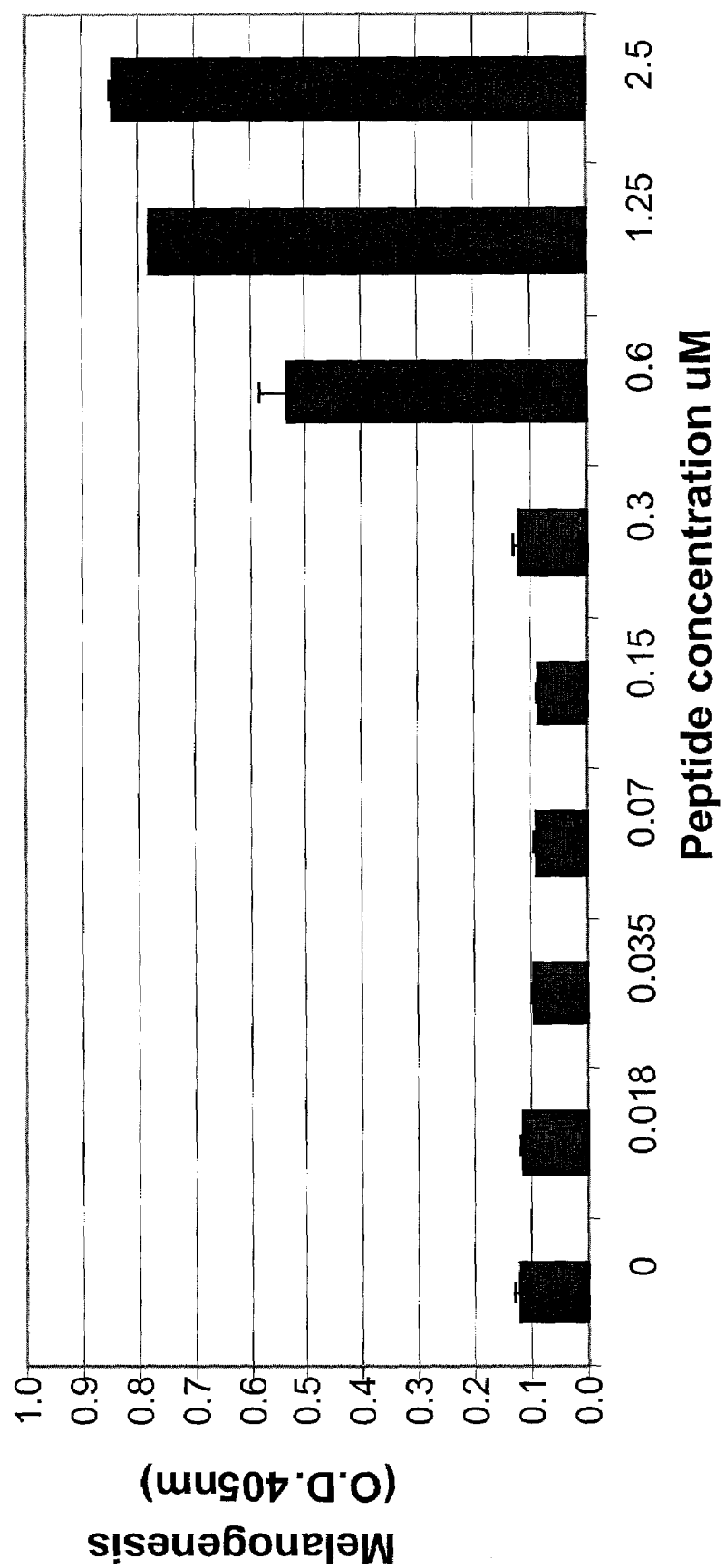
Figure 5D:
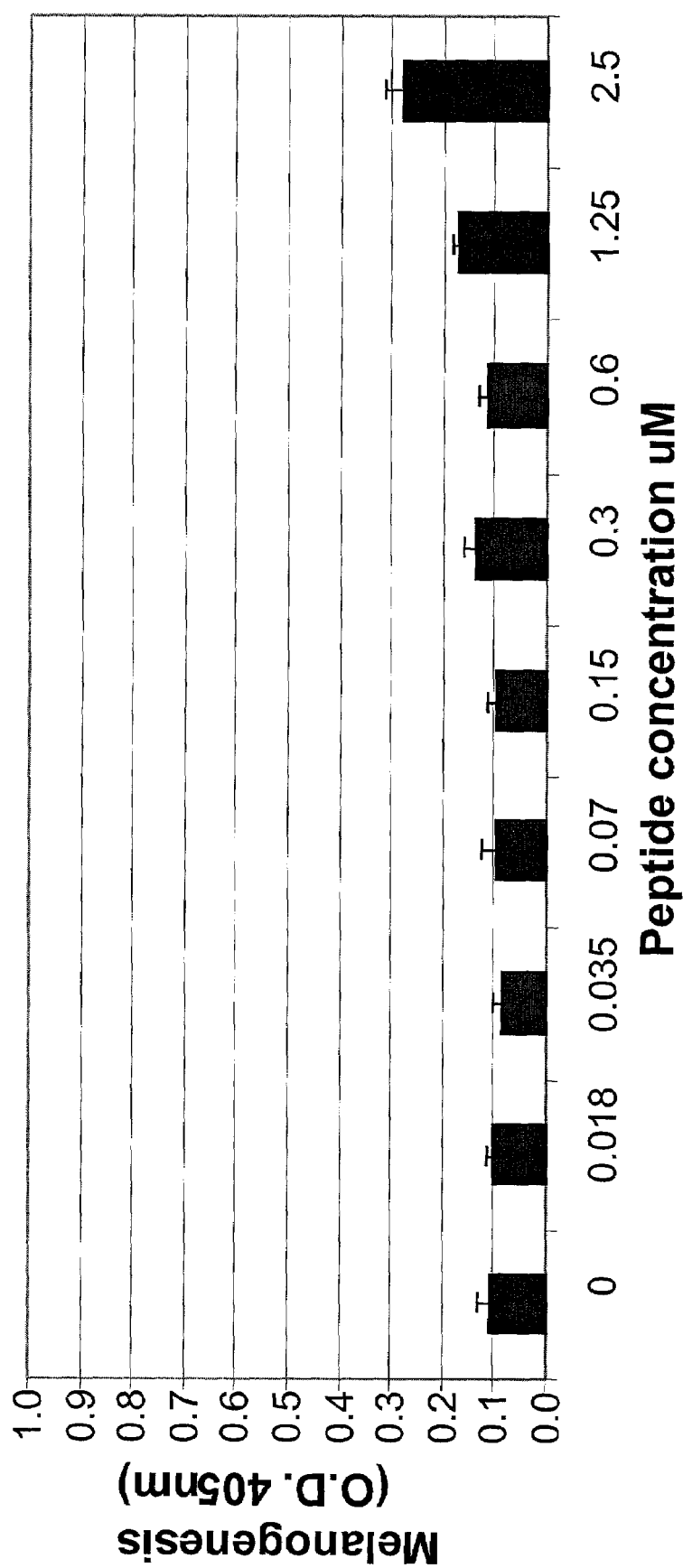
Figure 5E:
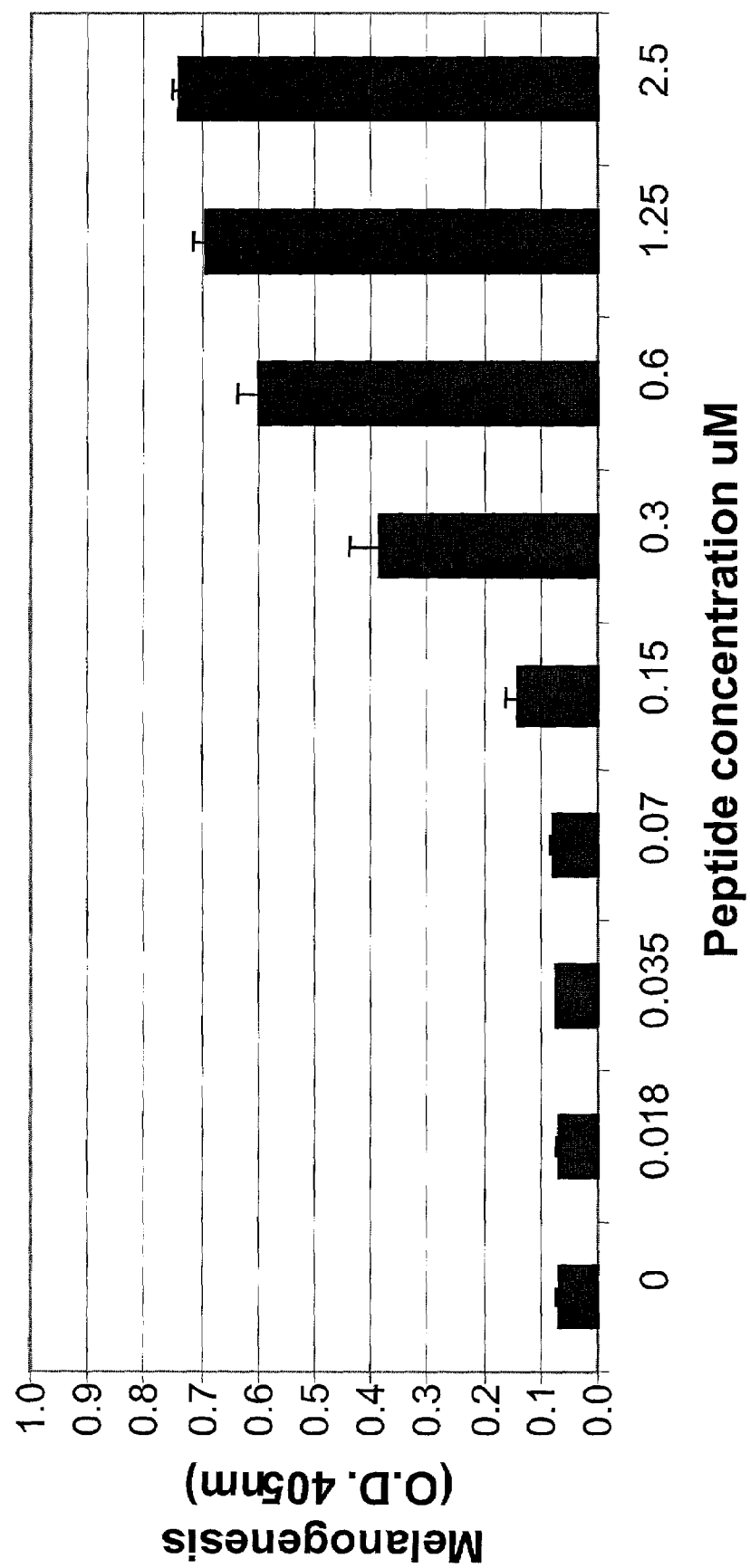
Figure 5F:
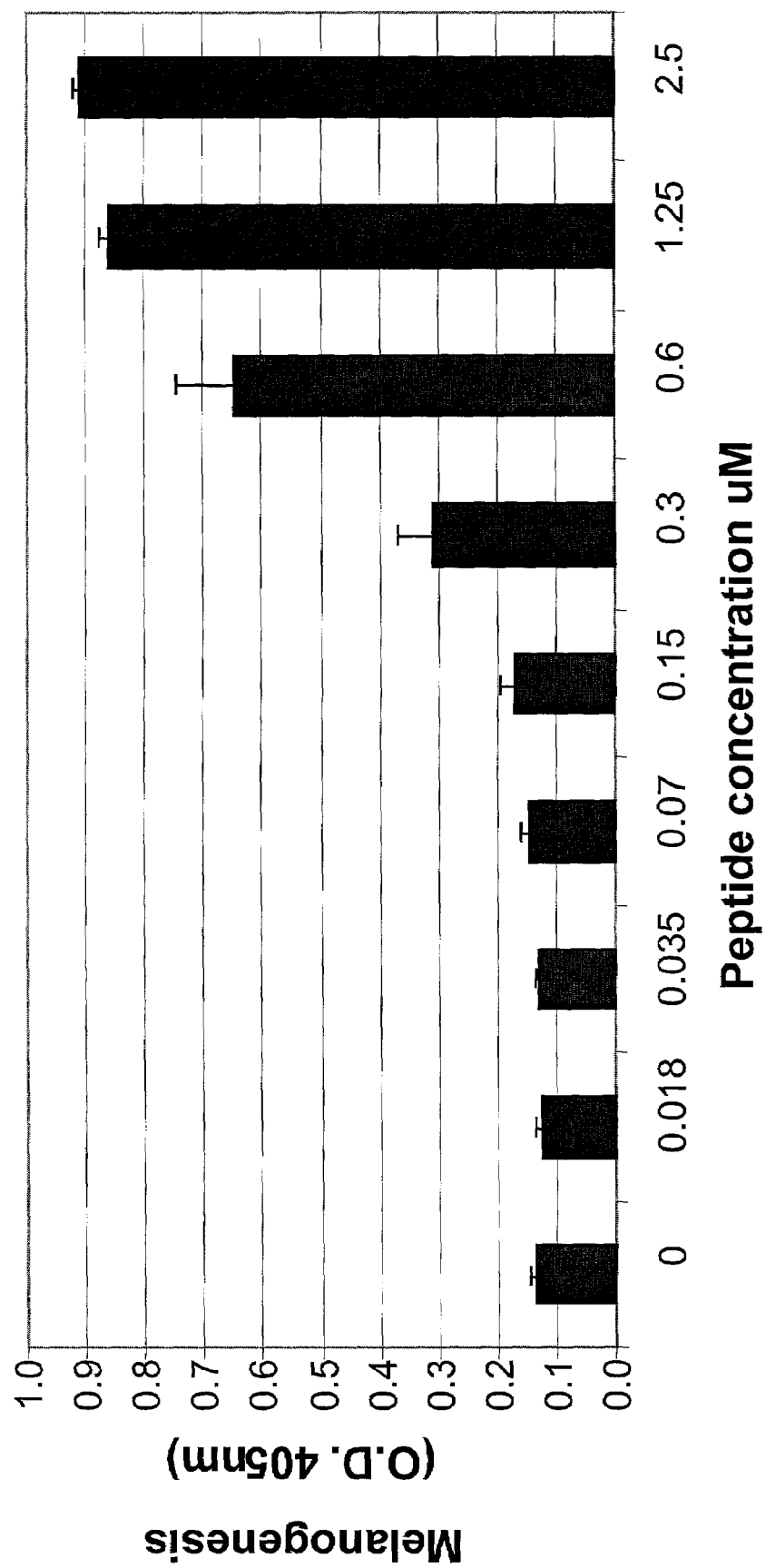
Figure 5G:
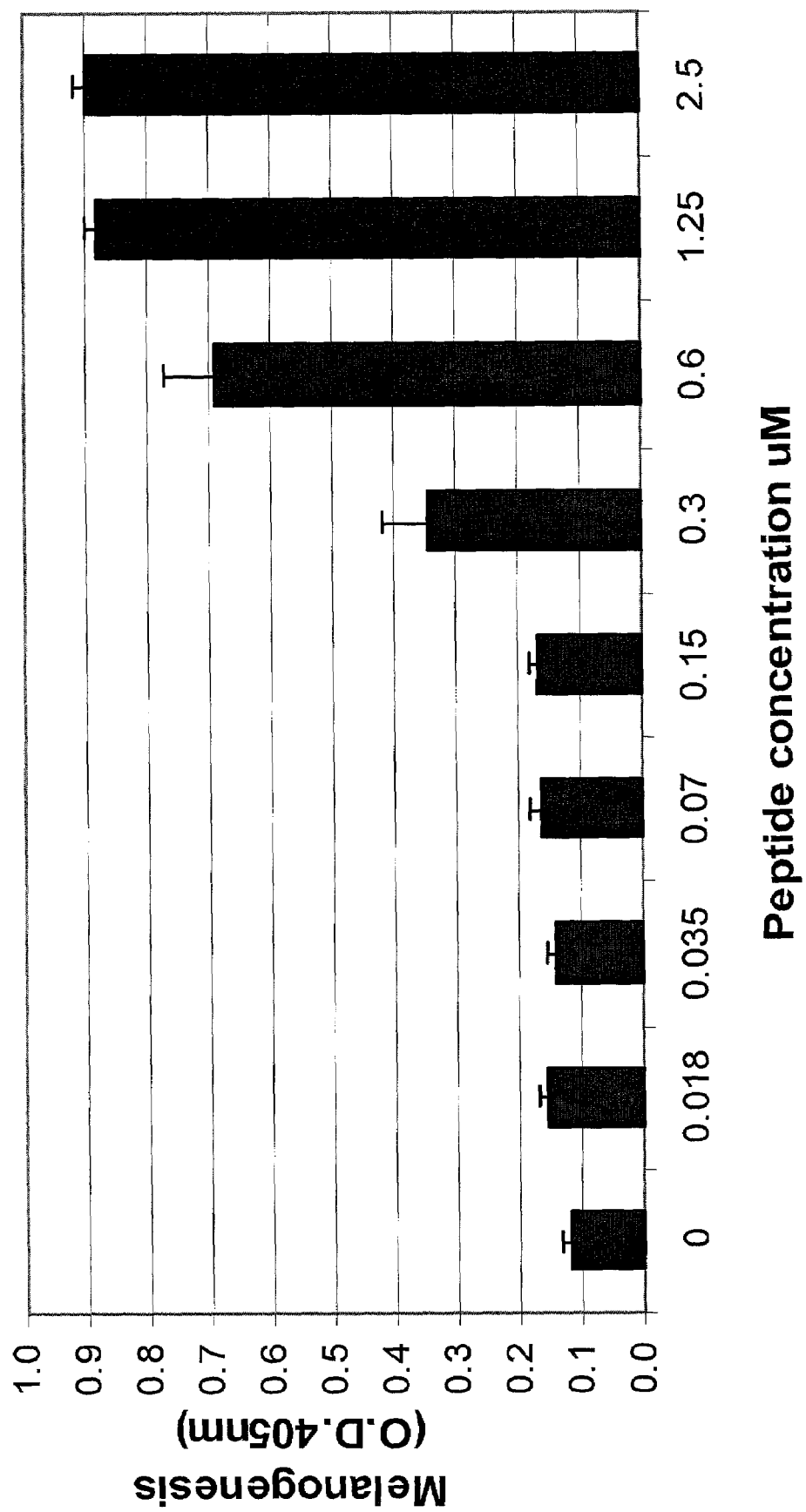

As can be seen from FIGS. 3 and 4, after a single injection of the compound comprising the GRK-derived peptide there was dramatic decrease in blood-glucose to the normal level (FIG. 3), while no change was observed in the controls (FIG. 4). Additionally, in the treated group, it was noted that 4 animals became normoglycemic already after the first injection (responders, FIG. 3), and the rest of the treated animals also became nornoglycemic after three additional weekly injections ("nonresponders", FIG. 3).

EXAMPLE 3

Measurement of Melanogenesis by Melanocytes in Cell Culture

Murine B16 melanoma cells were grown in DMEM +10% FCS+2mM Glutamine+100units/ml Penicillin+0.1 1mg/ml Streptomycin. The cells were incubated under controlled conditions (37° C., 5% $CO_2$).

The melanoma cells were plated in 96-well microtiter plates, 5,400 cells per well, and allowed to grow for 24 hours. Selected compounds comprising GRK-derived peptides were solubilized in DMSO and then diluted in PBS +0.1% BSA to 10X of the final concentration (see the procedure in Example 2).

Six different compounds comprising different GRK-derived peptides were added to the corresponding wells at the stated final concentrations (see FIGS. 5A–5F). The vehicle containing equal concentrations of DMSO, PBS and BSA was used as the control. The cells were then incubated for an additional 4-days, when dark melanin pigment accumulated in the wells of the treated cells.

Melanogenesis was then assessed by addition of 70 μl 1N NaOH per well to release all melanin from the cells and the optical density was determined by 405 nm, using an ELX-800 ELISA plate reader. Six wells were used for each concentration.

The results are shown in FIGS. 5A–5G. It can be seen from these graphs that significant melanogenesis occurred at peptide concentrations of 0.6 μM and, for some peptides, as low as 0.15 μM. It is readily apparent from these graphs that these peptides cause an enhancement in melanogenesis from melanocytes and that this effect is evident by rhe use of several different GRK-derived peptides.

EXAMPLE 4

Inhibition of Cyclic-AMP Production

It is well known that after activation of the various GPCRs there is an activation of the adenolate cyclase by G-proteins. This raises the cyclic-AMP levels in the cell, and these levels are then decreased due to the desensitization of the receptors by GRK. Thus it is expected that inhibition of GAST will eliminate this decrease in the cyclic AMP levels, and will cause a constitutive increase in cAMP levels.

C6 glioblastoma cells, which are known to express the β-adrenagic receptor (the substrate of GRK). have been used.

To the cells the following compounds were added:

| | |
|---|---|
| Group I: | Isoproteranol (ISO) (agonist of the β-adrenergic receptor) in concentrations of 1 μM and 10 μM; |
| Group II: | The compound of the invention KO24H107 (SEQ ID NO: 10) in concentrations of 1 μM and 10 μM; |
| Group III: | A combination of the peptide KO24H107 at a concentration of 10 μM and an hour later 1 μM isoproterenol; |
| Group IV: | A first addition of 1 μM isoproterenol and one hour later 10 μM of the compound of the invention KO24H107. |

The amount of the activity was measured by measuring the increase of intracellular cyclic AMP levels, which were measured using the commercially available kit of Biotrack Cellular Communication Assay cyclic-AMP enzyme—immunoassay (EIA) system.

Figure 6:
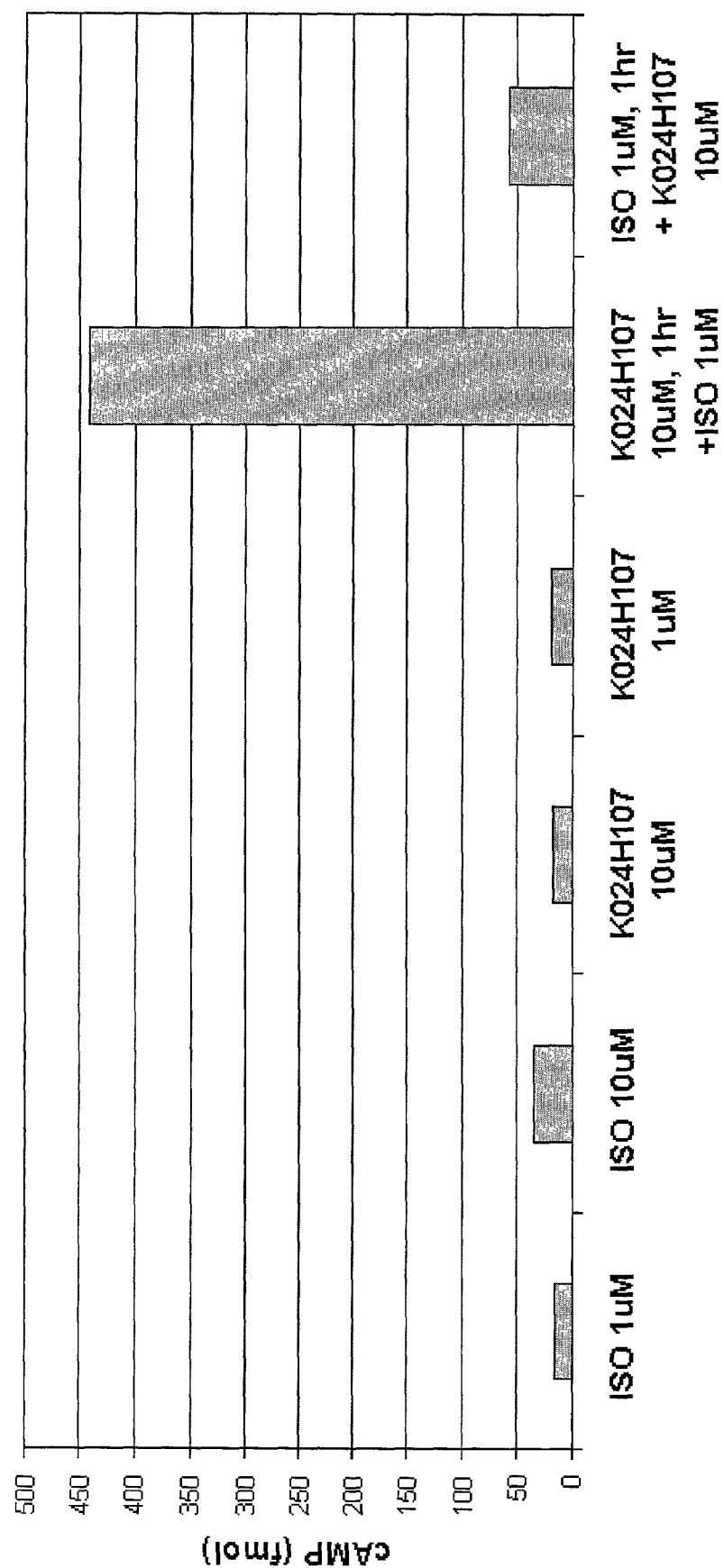
FIG. 6 shows the effect of the compound of the invention K024H107 on the production of cAMP, administered before or after activation by isoproteranol.

The results are shown in FIG. 6. As can be seen, the cyclic AMP levels rose significantly when initially the compound of the invention KO24H107 was added, and an hour later isoproterenol (activator of the receptor) was added. When the order of addition was reversed, the result was significantly different, the cyclic AMP level hardly changed, probably due to the fact that there is a lag in the activity of the compound of the invention due to the time required for penetration through cellular membranes. This experiment clearly indicates that the compounds of the invention are capable of significantly increasing the signal transduced by GPCR.

EXAMPLE 5

Activity of Compounds of the Invention on Reduction of Weight and Appetites of Normal Mice 18 Sabra male mice, 8 weeks old, were used and were divided into four groups as followed:

| | |
|---|---|
| Group I: | (n = 5) served as control and were injected with a vehicle which were 1.1% Tween80, 0.1% BSA, in DDW. |
| Group II: | (n = 4) were injected with NDP-αMSH, a known regulator of weight, in a concentration of 0.9 μg/kg BW; |
| Group III: | (n = 5) were injected with the compound of the invention KO24H107 at a concentration of 21 mg/kg body weight; |
| Group IV: | (n = 4) received a combination of NDP-αMSH and KO24H107 at the same concentration as above. |

The animals were weighed before trial and periodically during the trial.

At the same time, food was weighted before it was introduced into cages and at the end of each tested period. From this point on, the follow-up included both weighing of the mice and of the food for the short period, every couple of hours, until night, and later on for the long period, each 24 hour cycle. The results are shown in FIG. 7A and 7B.

Figure 7A:
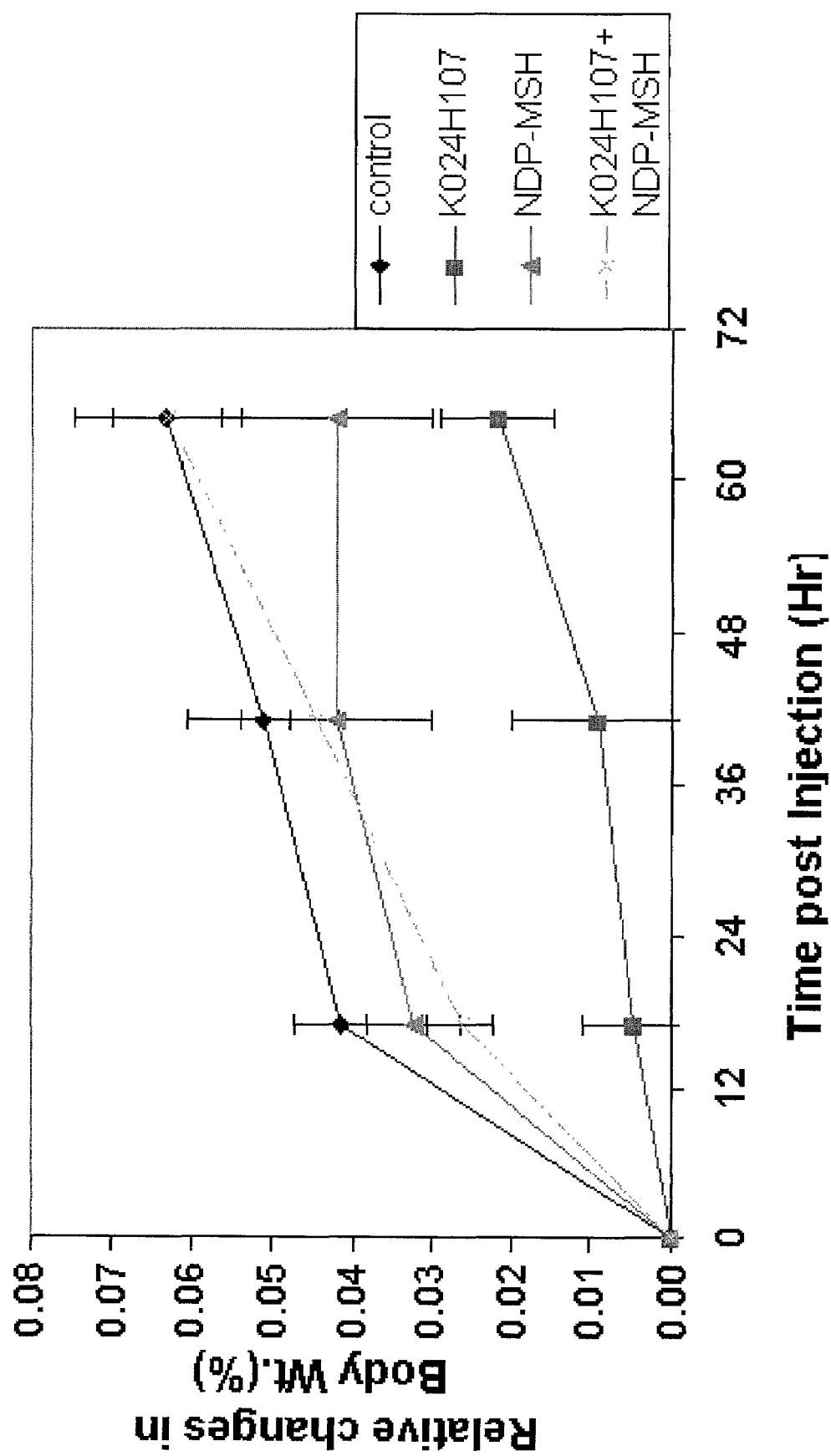
FIG. 7A shows the effect of compound K024H107 of the invention administered to normal mice on weight changes and FIG. 7B shows the effect of food consumption,.
Figure 7B:
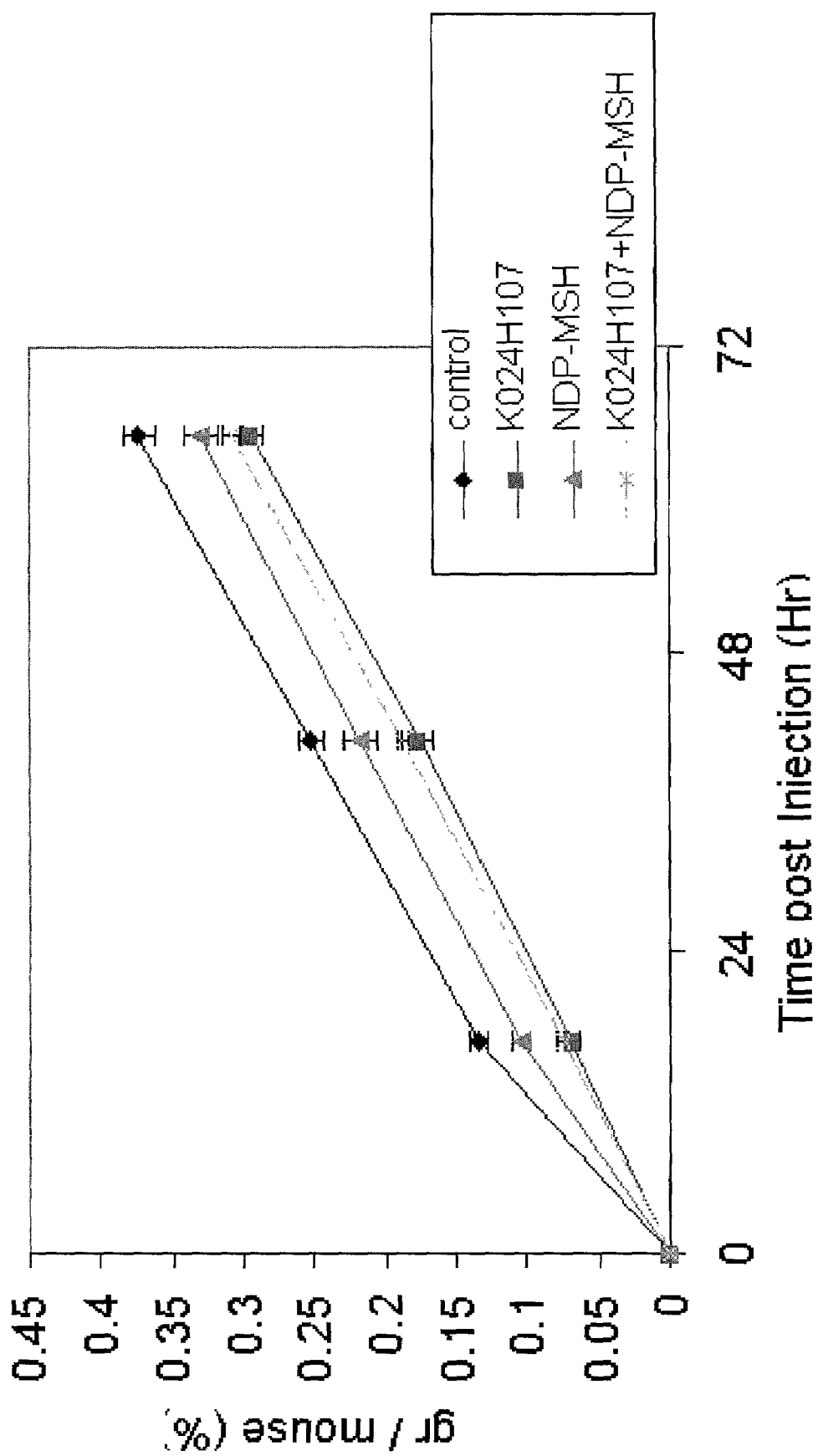

The results of FIG. 7A are shown as the percentage of change in body weight as compared to the initial weight for each mice, and then averaged for each group. The calculation of food consumption (FIG. 7B) was calculated in each group relative to the total weight of all animals (4 or 5 animals) and averaged separately for each group. As can be seen from the results, all three treated groups showed weight decrease and decrease in food consumption as compared to control. Group III treated with the compound of the invention alone showed the strongest effect.

The above experiment was conducted again with another compound comprising a GRK-derived peptide KO24H112 (SEQ ID NO:5) 16 animals were used as follows:

| | |
|---|---|
| Group I: | (n = 5) Vehicle as above; |
| Group II: | (N = 6) KO24H112 23.2 mg/kg; |
| Group III: | KO24H112 31.5 mg/kg. |

Figure 8A:
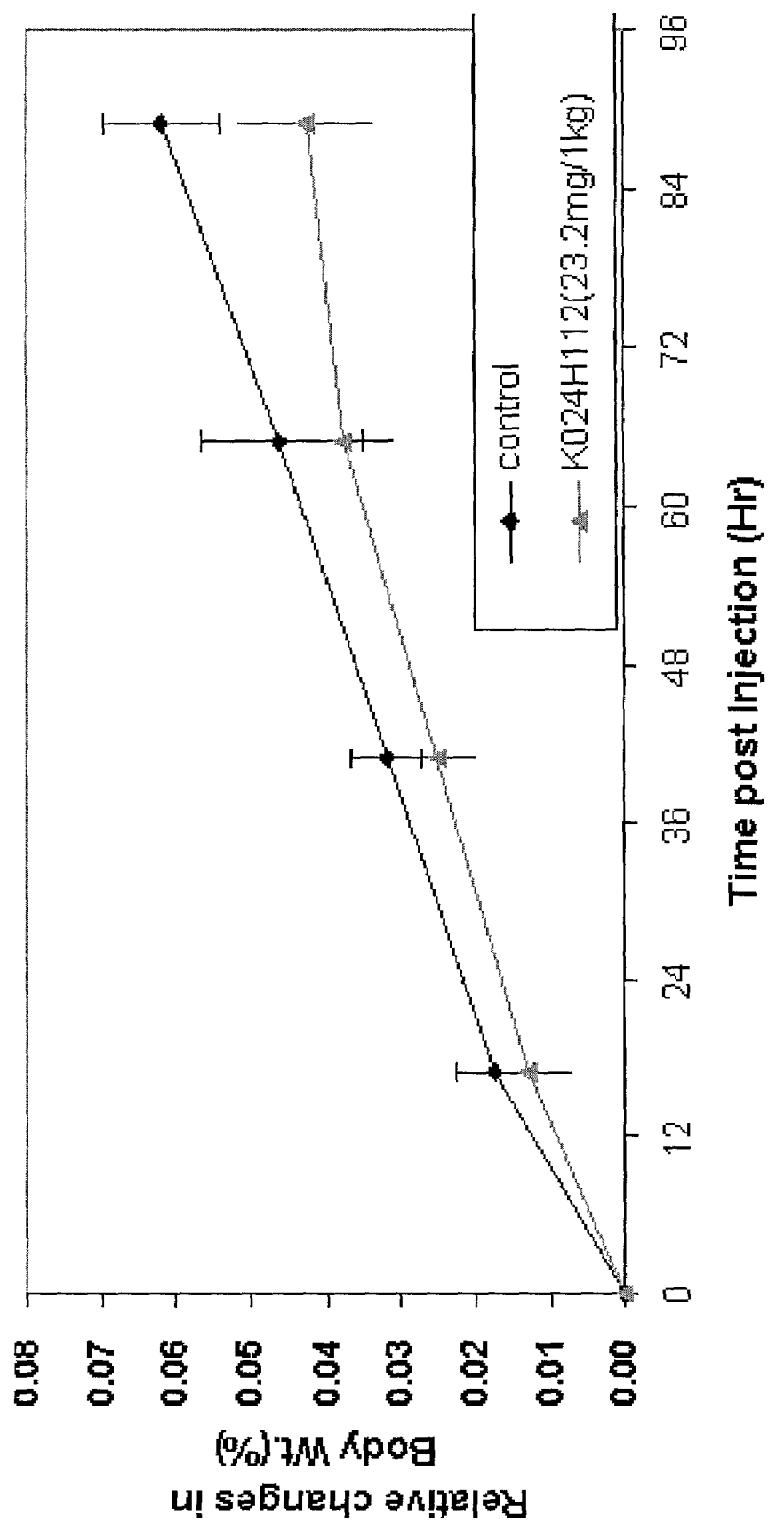
FIG. 8A shows the effect of the compound K024H112 administered to normal mice n on the weight and FIG. 8B shows the effect on food consumption of normal mice.
Figure 8B:
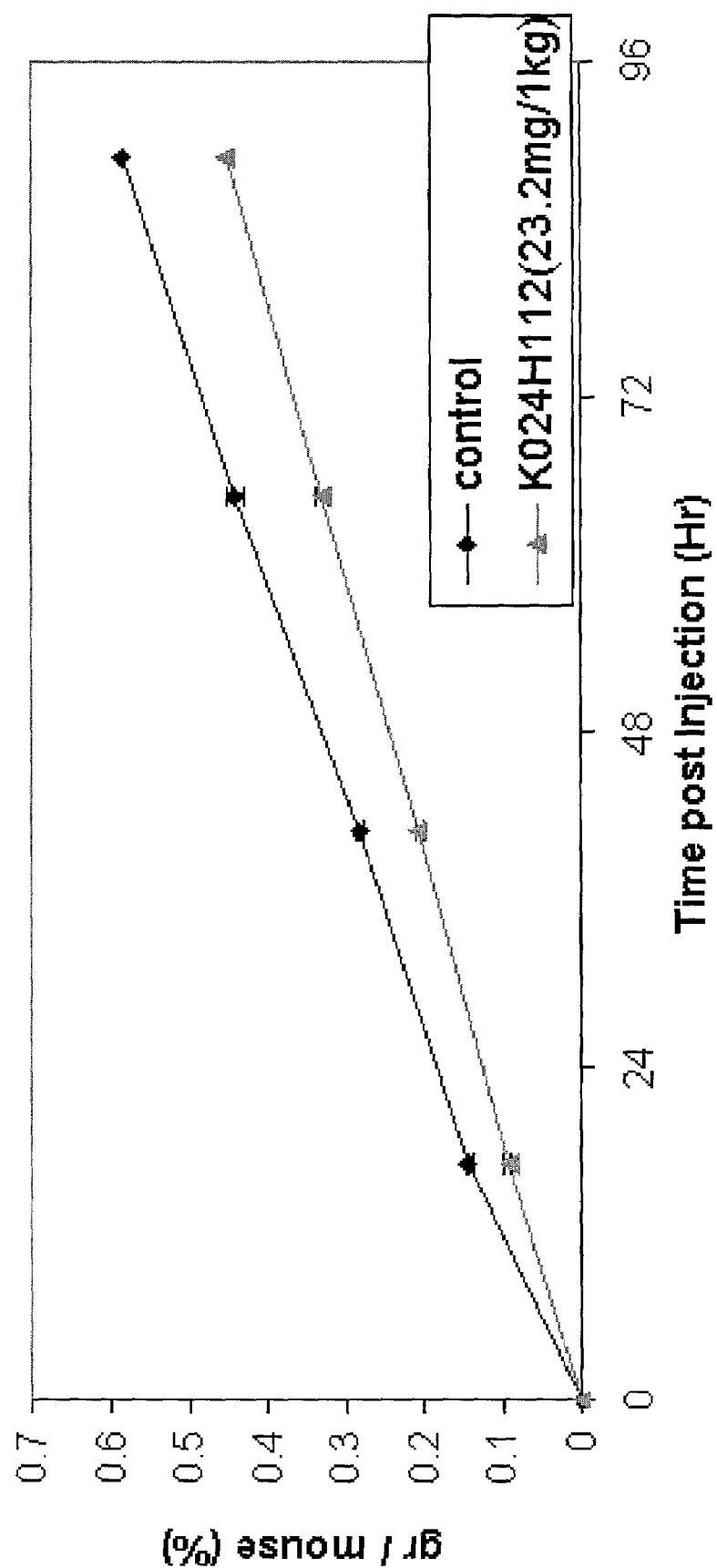

The results for weight change are shown in FIG. 8A and of change in food consumption are shown in FIG. 8B. As can be seen, this compound was also effective in reducing both body weight and consumption.

The above results indicated that two different compounds of the inventions comprising two different GRK-derived sequences were also effective in reducing both body weight and consumption.

The invention claimed is:

1. A method for modulating GRK-associated signal transduction in a subject in need thereof, comprising:
   administering to the subject an effective amount of a compound comprising a sequence selected from the group consisting of:
   (a) a sequence which is a continuous stretch of at least five amino acids present in GRK2 in positions 382–414 (HJ loop);
   (b) a variant of a sequence according to (a), wherein up to 20% of the amino acids of a native sequence have been replaced with a naturally or non-naturally occurring amino acid and/or up to 20% of the amino acids have their side-chains chemically modified and/or up to 20% of the amino acids have been deleted, provided that at least 50% of the amino acids present in the sequence of (a) are unaltered in the variant, and provided that the variant maintains the GRK-associated signal transduction property of the parent amino acid sequence of (a);
   (c) a sequence of any one of (a) to b, wherein at least one of the amino acids is replaced by the corresponding D-amino acid; and
   (d) a sequence being the sequence of any one of (a) to (c) in reverse order.

2. A method according to claim 1, wherein the compound comprises a sequence defined in 1(a).

3. The method of claim 1, wherein the compound is selected from the group consisting of: K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H108 (SEQ ID NO.: 11), K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), and a compound comprising the sequences of any one of SEQ ID NOS: 20 to SEQ ID NO:38.

4. The method according to claim 1, wherein the compound comprises a moiety for transfer across cell membranes in association with the sequence of any one of (a) to (d).

5. A method according to claim 4, wherein the moiety is a hydrophobic moiety.

6. A method according to claim 1, wherein the subject in need is suffering from a disease selected from the group consisting of diabetes, hypertension, obesity, dislipidemia, congestive heart disease, arteriosclerosis, cholesterolinemia, coagulation disorders and syndrome X.

7. A method according to claim 6, wherein the subject in need has diabetes mellitus Type II.

8. A method for the treatment of diabetic-associated phenomena in a subject comprising administering to the subject a therapeutically effective amount of a modulator of GRK-associated signal transduction (GAST).

9. The method of claim 8, wherein the GAST modulator is an inhibitor selected from the group consisting of:
   (i) a compound comprising a sequence selected from the group consisting of:
   (1) a sequence which is a continuous stretch of at least five amino acids present in GRK2 in positions 382–414 (HJ loop);
   (2) a variant of a sequence according to (1), wherein up to 20% amino acids of a native sequence have been replaced with a naturally or non-naturally occurring amino acid and/or up to 20% of the amino acids have their side chains chemically modified and/or up to 20% of the amino acids have been deleted, provided that at least 50% of the amino acids present in the sequence of (1) are unaltered in the variant and provided that the variant maintains the GRK-associated signal transduction of the parent amino acid sequence of (1);
   (3) a sequence of any one of (1) to (2), wherein at least one of the amino acids is replaced by the corresponding D-amino acid; and
   (4) a sequence being the sequence of any one of (1) to (3) in reverse order.

10. The method of claim 9, wherein said compound (i) is selected from the group consisting of: K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H108 (SEQ ID NO.: 11), K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), and a compound comprising any one of the sequences of SEQ ID NO: 20 to SEQ ID NO:38.

11. A method according to claim 8, wherein the diabetic-associated phenomena is selected from the group consisting of diabetes type I, diabetes type II, diabetic associated obesity, diabetic associated hypertension, and diabetic associated dislipidemia.

12. A method according to claim 11, for the treatment of diabetes mellitus Type II.

13. A pharmaceutical composition comprising a pharmaceutically acceptable carrier and a compound selected from the group consisting of:
   (a) a sequence which is a continuous stretch of at least five amino acids present in GRK2 in positions 382–414 (HJ loop);
   (b) a variant of a sequence according to (a), wherein up to 20% of the amino acids of a native sequence have been replaced with a naturally or non-naturally occurring amino acid and/or up to 20% of the amino acids have their side chains chemically modified and/or up to 20% of the amino acids have been deleted, provided that at least 50% of the amino acids present in the sequence of (a) are unaltered in the variant and provided that the variant maintains the GRK-associated signal transduction of the parent amino acid sequence of (a);
   (c) a sequence of any one of (a) to (b), wherein at least one of the amino acids is replaced by the corresponding D-amino acid; and
   (d) a sequence being the sequence of any one of (a) to (c) in reverse order.

14. The pharmaceutical composition according to claim 13, wherein the compound comprises a sequence of (a), (b), (c), and (d).

15. The pharmaceutical composition according to claim 13, wherein the compound is selected from the group consisting of: K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H108 (SEQ ID NO.: 11), K024H109 (SEQ ID NO.: 12), K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), and a compound comprising s sequence selected from the sequence of SEQ ID NO: 20 to SEQ ID NO:38.

16. The pharmaceutical composition according to claim 13, wherein the compound comprises a moiety for transfer across cell membranes in association with the sequence of any one of (a) to (d).

17. The pharmaceutical composition according to claim 16, wherein the moiety is a hydrophobic moiety.

18. A method in accordance with claim 1, wherein the subject in which the compound is administered is being treated for weight and appetite reduction.

19. A method in accordance with claim 1, wherein the subject in which the compound is administered is being treated for modulation of melanogenesis.

20. The method of claim 3, wherein the compound is K024H107 (SEQ ID NO:10).

21. The method of claim 10, wherein the compound is K024H107 (SEQ ID NO:10).

22. The pharmaceutical composition according to claim 15, wherein the compound is K024H107 (SEQ ID NO:10).

23. A composition comprising a carrier and a compound selected from the group consisting of:
   (a) a sequence which is a continuous stretch of at least five amino acids present in GRK2 in positions 382–414 (HJ loop);
   (b) a variant of a sequence according to (a), wherein up to 20% of the amino acids of a native sequence have been replaced with a naturally or non-naturally occurring amino acid and/or up to 20% of the amino acids have their side chains chemically modified and/or up to 20% of the amino acids have been deleted, provided that at least 50% of the amino acids present in the sequence of (a) are unaltered in the variant and provided that the variant maintains the GRK-associated signal transduction of the parent amino acid sequence of (a);
   (c) a sequence of any one of (a) to (b), wherein at least one of the amino acids is replaced by the corresponding D-amino acid; and
   (d) a sequence being the sequence of any one of (a) to (c) in reverse order.

24. The composition according to claim 23, wherein the compound is selected from the group consisting of: K024H003 (SEQ ID NO.: 2), K024H007 (SEQ ID NO.: 3), K024H101 (SEQ ID NO.: 4), K024H102 (SEQ ID NO.: 5), K024H103 (SEQ ID NO.: 6), K024H104 (SEQ ID NO.: 7), K024H105 (SEQ ID NO.: 8), K024H106 (SEQ ID NO.: 9), K024H107 (SEQ ID NO.: 10), K024H108 (SEQ ID NO.: 11), K024H109 (SEQ ID NO.: 12),.K024H110 (SEQ ID NO.: 13), K024H111 (SEQ ID NO.: 14), K024H112 (SEQ ID NO.: 15), K024H113 (SEQ ID NO.: 16), K024H114 (SEQ ID NO.: 17), K024H901 (SEQ ID NO.: 18), and K024H903 (SEQ ID NO.: 19), and a compound comprising s sequence selected from the sequence of SEQ ID NO: 20 to SEQ ID NO:38.

25. The pharmaceutical composition according to claim 23, wherein the compound comprises a moiety for transfer across cell membranes in association with the sequence of any one of (a) to (d).

26. The pharmaceutical composition according to claim 25, wherein the moiety is a hydrophobic moiety.

27. A method according to claim 1, wherein the compound comprises a sequence defined in 1(b).

28. A method according to claim 1, wherein the compound comprises a sequence defined in 1(c).

29. A method according to claim 1, wherein the compound comprises a sequence defined in 1(d).

* * * * *

SEQUENCE LISTING

```
<160> NUMBER OF SEQ ID NOS: 41

<210> SEQ ID NO 1
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: ACETYLATION
<222> LOCATION: (1)...(0)
<220> FEATURE:
<221> NAME/KEY: AMIDATION
<222> LOCATION: (0)...(6)

<400> SEQUENCE: 1

Leu Leu Arg Gly His Ser
1               5

<210> SEQ ID NO 2
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: ACETYLATION
<222> LOCATION: (1)...(0)
<223> OTHER INFORMATION: D-isomer at position 4
<220> FEATURE:
<221> NAME/KEY: AMIDATION
<222> LOCATION: (0)...(6)

<400> SEQUENCE: 2

Leu Leu Arg Lys His Ser
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: ACETYLATION
<222> LOCATION: (1)...(0)
<223> OTHER INFORMATION: D-isomer at position 4
<220> FEATURE:
<221> NAME/KEY: AMIDATION
<222> LOCATION: (0)...(6)

<400> SEQUENCE: 3

Leu Leu Arg Arg His Ser
 1               5

<210> SEQ ID NO 4
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<220> FEATURE:
<221> NAME/KEY: AMIDATION
<222> LOCATION: (0)...(6)

<400> SEQUENCE: 4

Leu Leu Arg Gly His Ser
 1               5

<210> SEQ ID NO 5
<211> LENGTH: 9
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<220> FEATURE:
<221> NAME/KEY: AMIDATION
<222> LOCATION: (0)...(9)

<400> SEQUENCE: 5

Leu Leu Arg Gly His Ser Pro Phe Arg
 1               5

<210> SEQ ID NO 6
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(6)

<400> SEQUENCE: 6

Leu Leu Arg Lys His Ser
 1               5
```

```
<210> SEQ ID NO 7
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(6)

<400> SEQUENCE: 7

Leu Leu Arg Glu His Ser
1               5

<210> SEQ ID NO 8
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<220> FEATURE:
<221> NAME/KEY: AMIDATION
<222> LOCATION: (0)...(6)

<400> SEQUENCE: 8

Leu Leu Arg Tyr His Ser
1               5

<210> SEQ ID NO 9
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer a position 4
<220> FEATURE:
<221> NAME/KEY: AMIDATION
<222> LOCATION: (0)...(6)

<400> SEQUENCE: 9

Leu Leu Arg Leu His Ser
1               5

<210> SEQ ID NO 10
<211> LENGTH: 6
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(6)

<400> SEQUENCE: 10

Leu Leu Arg Arg His Ser
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
      Position 7 is biotinylated
<220> FEATURE:
<221> NAME/KEY: AMIDATION
<222> LOCATION: (0)...(7)

<400> SEQUENCE: 11

Leu Leu Arg Arg His Ser Lys
 1               5

<210> SEQ ID NO 12
<211> LENGTH: 7
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(7)

<400> SEQUENCE: 12

Leu Leu Arg Lys His Ser Pro
 1               5

<210> SEQ ID NO 13
<211> LENGTH: 9
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(9)

<400> SEQUENCE: 13

Leu Leu Arg Arg His Ser Ile Val Thr
 1               5

<210> SEQ ID NO 14
<211> LENGTH: 8
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(8)

<400> SEQUENCE: 14

Leu Leu Arg Arg His Ser Ile Val
 1               5
```

```
<210> SEQ ID NO 15
<211> LENGTH: 7
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
<220> FEATURE:
<221> NAME/KEY: AMIDATION
<222> LOCATION: (0)...(7)

<400> SEQUENCE: 15

Leu Leu Arg Arg His Ser Ile
1               5

<210> SEQ ID NO 16
<211> LENGTH: 7
<212> TYPE: PRT
<213> ORGANISM: Artificial Sequence
<220> FEATURE:
<223> OTHER INFORMATION: bARK1
<220> FEATURE:
<221> NAME/KEY: MYRISTATE
<222> LOCATION: (1)...(0)
<223> OTHER INFORMATION: D-isomer at position 4
    Benzoylamide at position 7
<220> FEATURE:
<221> NAME/KEY: AMIDATION
<222> LOCATION: (0)...(7)

<400> SEQUENCE: 16

Leu Leu Arg Arg His Ser Lys
1               5

<210> SEQ ID NO 17
<211> LENGTH: 7
<212> TYPE: PRT
<213> ORGANISM: Artificial Sequence
<220> FEATURE:
<223> OTHER INFORMATION: bARK1
    Oleyl at position 1
    D-isomer at position 4
    Benzoylamide at position 7
<220> FEATURE:
<221> NAME/KEY: AMIDATION
<222> LOCATION: (0)...(7)

<400> SEQUENCE: 17

Leu Leu Arg Arg His Ser Lys
1               5

<210> SEQ ID NO 18
<211> LENGTH: 6
<212> TYPE: PRT
<213> ORGANISM: Artificial Sequence
<220> FEATURE:
<223> OTHER INFORMATION: bARK1
    Strearate at position 1
<220> FEATURE:
<221> NAME/KEY: AMIDATION
<222> LOCATION: (0)...(6)

<400> SEQUENCE: 18

Leu Leu Arg Gly His Ser
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: bARK1
      Stearate at position 1
      D-isomer at position 4
<220> FEATURE:
<221> NAME/KEY: AMIDATION
<222> LOCATION: (0)...(6)

<400> SEQUENCE: 19

Leu Leu Arg Lys His Ser
 1               5

<210> SEQ ID NO 20
<211> LENGTH: 32
<212> TYPE: PRT
<213> ORGANISM: Artificial Sequence
<220> FEATURE:
<223> OTHER INFORMATION: synthetic

<400> SEQUENCE: 20

Phe Lys Leu Leu Arg Gly His Ser Pro Phe Arg Gln His Lys Thr Asp
 1               5                  10                  15

Lys His Glu Ile Asp Arg Met Thr Leu Thr Met Ala Val Glu Leu Pro
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: synthetic

<400> SEQUENCE: 21

Phe Lys Leu Leu Arg Gly His Ser Pro Phe Arg Gln His Lys Thr Asp
 1               5                  10                  15

Lys His Glu Ile Asp Arg Met Thr Leu Thr Val Asn Val Glu Leu Pro
            20                  25                  30

<210> SEQ ID NO 22
<211> LENGTH: 20
<212> TYPE: PRT
<213> ORGANISM: Artificial Sequence
<220> FEATURE:
<223> OTHER INFORMATION: GRK2

<400> SEQUENCE: 22

Leu Asp Leu Met Asn Gly Gly Asp Leu His Tyr His Leu Ser Gln His
 1               5                  10                  15

Gly Val Phe Ser
            20

<210> SEQ ID NO 23
<211> LENGTH: 20
<212> TYPE: PRT
<213> ORGANISM: Artificial Sequence
<220> FEATURE:
<223> OTHER INFORMATION: GRK3

<400> SEQUENCE: 23

Leu Asp Leu Met Asn Gly Gly Asp Leu His Tyr His Leu Ser Gln His
 1               5                  10                  15

Gly Val Phe Ser
```

<210> SEQ ID NO 24
<211> LENGTH: 9
<212> TYPE: PRT
<213> ORGANISM: Artificial Sequence
<220> FEATURE:
<223> OTHER INFORMATION: GRK2

<400> SEQUENCE: 24

Met Ser Tyr Ala Phe His Thr Pro Asp
1               5

<210> SEQ ID NO 25
<211> LENGTH: 9
<212> TYPE: PRT
<213> ORGANISM: Artificial Sequence
<220> FEATURE:
<223> OTHER INFORMATION: GRK3

<400> SEQUENCE: 25

Met Thr Tyr Ala Phe His Thr Pro Asp
1               5

<210> SEQ ID NO 26
<211> LENGTH: 21
<212> TYPE: PRT
<213> ORGANISM: Artificial Sequence
<220> FEATURE:
<223> OTHER INFORMATION: GRK2

<400> SEQUENCE: 26

Arg Ile Met Leu Ser Leu Val Ser Thr Gly Asp Cys Pro Phe Ile Val
1               5                   10                  15

Cys Met Ser Tyr Ala
            20

<210> SEQ ID NO 27
<211> LENGTH: 21
<212> TYPE: PRT
<213> ORGANISM: Artificial Sequence
<220> FEATURE:
<223> OTHER INFORMATION: GRK3

<400> SEQUENCE: 27

Arg Ile Met Leu Ser Leu Val Ser Thr Gly Asp Cys Pro Phe Ile Val
1               5                   10                  15

Cys Met Thr Tyr Ala
            20

<210> SEQ ID NO 28
<211> LENGTH: 11
<212> TYPE: PRT
<213> ORGANISM: Artificial Sequence
<220> FEATURE:
<223> OTHER INFORMATION: Myristylistyl at position 1

<400> SEQUENCE: 28

Gly Gly Arg Gly His Ser Pro Phe Arg Gln His
1               5                   10

<210> SEQ ID NO 29
<211> LENGTH: 10
<212> TYPE: PRT
<213> ORGANISM: Artificial Sequence
<220> FEATURE:

<223> OTHER INFORMATION: Myristylistyl at position 1

<400> SEQUENCE: 29

Gly Gly Arg Gly His Ser Pro Phe Arg Gln
 1               5                   10

<210> SEQ ID NO 30
<211> LENGTH: 9
<212> TYPE: PRT
<213> ORGANISM: Artificial Sequence
<220> FEATURE:
<223> OTHER INFORMATION: Myristylistyl at position 1

<400> SEQUENCE: 30

Gly Gly Arg Gly His Ser Pro Phe Arg
 1               5

<210> SEQ ID NO 31
<211> LENGTH: 9
<212> TYPE: PRT
<213> ORGANISM: Artificial Sequence
<220> FEATURE:
<223> OTHER INFORMATION: Myristylistyl at position 1

<400> SEQUENCE: 31

Gly Gly His Ser Pro Phe Arg Gln His
 1               5

<210> SEQ ID NO 32
<211> LENGTH: 8
<212> TYPE: PRT
<213> ORGANISM: Artificial Sequence
<220> FEATURE:
<223> OTHER INFORMATION: Myristylistyl at position 1

<400> SEQUENCE: 32

Gly Gly His Ser Pro Phe Arg Gln
 1               5

<210> SEQ ID NO 33
<211> LENGTH: 9
<212> TYPE: PRT
<213> ORGANISM: Artificial Sequence
<220> FEATURE:
<223> OTHER INFORMATION: Myristylistyl at position 1

<400> SEQUENCE: 33

Gly Gly Pro Phe Arg Gln His Lys Thr
 1               5

<210> SEQ ID NO 34
<211> LENGTH: 9
<212> TYPE: PRT
<213> ORGANISM: Artificial Sequence
<220> FEATURE:
<223> OTHER INFORMATION: Myristylistyl at position 1

<400> SEQUENCE: 34

Gly Gly Phe Arg Gln His Lys Thr Lys
 1               5

<210> SEQ ID NO 35
<211> LENGTH: 8
<212> TYPE: PRT
<213> ORGANISM: Artificial Sequence
<220> FEATURE:
<223> OTHER INFORMATION: Myristylistyl at position 1

```
<400> SEQUENCE: 35

Gly Leu Leu Arg His Arg Ser Ile
1               5

<210> SEQ ID NO 36
<211> LENGTH: 8
<212> TYPE: PRT
<213> ORGANISM: Artificial Sequence
<220> FEATURE:
<223> OTHER INFORMATION: Myristylistyl at position 1

<400> SEQUENCE: 36

Gly Leu Leu Arg His Arg Ala Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Myristylistyl at position 1

<400> SEQUENCE: 37

Gly Leu Leu Arg Arg His Ser Ile
1               5

<210> SEQ ID NO 38
<211> LENGTH: 8
<212> TYPE: PRT
<213> ORGANISM: Artificial Sequence
<220> FEATURE:
<223> OTHER INFORMATION: Lauryl at position 1

<400> SEQUENCE: 38

Gly Leu Leu Arg Arg His Ser Ile
1               5

<210> SEQ ID NO 39
<211> LENGTH: 30
<212> TYPE: DNA
<213> ORGANISM: Artificial Sequence
<220> FEATURE:
<223> OTHER INFORMATION: GRK2

<400> SEQUENCE: 39
ctcggcctcg ggcgcggccg agcgccgcgc                              30

<210> SEQ ID NO 40
<211> LENGTH: 30
<212> TYPE: DNA
<213> ORGANISM: Artificial Sequence
<220> FEATURE:
<223> OTHER INFORMATION: GRK3

<400> SEQUENCE: 40
caagcttcat ctgtatttac agctgctcgc                              30

<210> SEQ ID NO 41
<211> LENGTH: 20
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
```

-continued

```
<223> OTHER INFORMATION: Xaa is Phe, Tyr or Trp
<220> FEATURE:
<221> NAME/KEY: misc_feature
<222> LOCATION: (2)..(2)
<223> OTHER INFORMATION: Xaa is Lys or Ornithine
<220> FEATURE:
<221> NAME/KEY: misc_feature
<222> LOCATION: (3)..(3)
<223> OTHER INFORMATION: Xaa is Leu, Ile, Met or Val
<220> FEATURE:
<221> NAME/KEY: misc_feature
<222> LOCATION: (4)..(4)
<223> OTHER INFORMATION: Xaa is Ile, Leu, Met or Val
<220> FEATURE:
<221> NAME/KEY: misc_feature
<222> LOCATION: (5)..(5)
<223> OTHER INFORMATION: Xaa is Arg or Lys
<220> FEATURE:
<221> NAME/KEY: misc_feature
<222> LOCATION: (6)..(6)
<223> OTHER INFORMATION: Xaa is Gly or Ala
<220> FEATURE:
<221> NAME/KEY: misc_feature
<222> LOCATION: (8)..(8)
<223> OTHER INFORMATION: Xaa is Ser or Thr
<220> FEATURE:
<221> NAME/KEY: misc_feature
<222> LOCATION: (10)..(10)
<223> OTHER INFORMATION: Xaa is Phe, Tyr or Trp
<220> FEATURE:
<221> NAME/KEY: misc_feature
<222> LOCATION: (11)..(11)
<223> OTHER INFORMATION: Xaa is Arg or Lys
<220> FEATURE:
<221> NAME/KEY: misc_feature
<222> LOCATION: (12)..(12)
<223> OTHER INFORMATION: Xaa is Gln, Glu, Asp, Asn, or a substituted or
      unsubstituted aliphatic, benzylic or aromatic ester of glutamic
      acid or of aspartic acid
<220> FEATURE:
<221> NAME/KEY: misc_feature
<222> LOCATION: (14)..(14)
<223> OTHER INFORMATION: Xaa is Lys or Ornithine
<220> FEATURE:
<221> NAME/KEY: misc_feature
<222> LOCATION: (15)..(15)
<223> OTHER INFORMATION: Xaa is Thr or Ser
<220> FEATURE:
<221> NAME/KEY: misc_feature
<222> LOCATION: (16)..(16)
<223> OTHER INFORMATION: Xaa is Lys or Ornithine
<220> FEATURE:
<221> NAME/KEY: misc_feature
<222> LOCATION: (17)..(17)
<223> OTHER INFORMATION: Xaa is Asp, Asn, a substituted or unsubstituted
      aliphatic, benzylic or aromatic ester of aspartic acid, Gln, Glu,
      or a substituted or unsubstituted aliphatic, benzylic or aromatic
      ester of glutamic acid
<220> FEATURE:
<221> NAME/KEY: misc_feature
<222> LOCATION: (18)..(18)
<223> OTHER INFORMATION: Xaa is Lys or Ornithine
<220> FEATURE:
<221> NAME/KEY: misc_feature
<222> LOCATION: (20)..(20)
<223> OTHER INFORMATION: Xaa is Glu, Gln, Asn, Asp, or a substituted or
      unsubstituted aliphatic, benzylic or aromatic ester of aspartic
      acid or of glutamic acid

<400> SEQUENCE: 41

Xaa Xaa Xaa Xaa Xaa Xaa His Xaa Phe Xaa Xaa Xaa His Xaa Xaa Xaa
1               5                   10                  15

Xaa Xaa His Xaa
            20
```